(12) United States Patent
Maier et al.

(10) Patent No.: US 7,697,576 B2
(45) Date of Patent: Apr. 13, 2010

(54) CYTOLOGICAL ANALYSIS BY RAMAN SPECTROSCOPIC IMAGING

(75) Inventors: John S. Maier, Pittsburgh, PA (US); Joseph E. Demuth, Pittsburgh, PA (US); Jeffrey K. Cohen, Pittsburgh, PA (US); Shona Stewart, Pittsburgh, PA (US); Lindy A. McClelland, Pittsburgh, PA (US)

(73) Assignee: Chem Image Corporation, Pittsburgh, PA (US)

( * ) Notice: Subject to any disclaimer, the term of this patent is extended or adjusted under 35 U.S.C. 154(b) by 92 days.

(21) Appl. No.: 11/000,591

(22) Filed: Nov. 30, 2004

(65) Prior Publication Data

US 2005/0277816 A1    Dec. 15, 2005

Related U.S. Application Data

(60) Provisional application No. 60/568,357, filed on May 5, 2004.

(51) Int. Cl.
*H01S 3/00* (2006.01)
(52) U.S. Cl. .......................................................... 372/3
(58) Field of Classification Search ...................... None
See application file for complete search history.

(56) References Cited

U.S. PATENT DOCUMENTS

| | | | |
|---|---|---|---|
| 5,991,653 A | | 11/1999 | Richards-Kortum et al. |
| 6,002,476 A | * | 12/1999 | Treado .................. 356/301 |
| 6,095,982 A | | 8/2000 | Richards-Kortum et al. |
| 6,174,291 B1 | | 1/2001 | McMahon et al. |
| 6,449,087 B2 | * | 9/2002 | Ogino .................. 359/383 |
| 6,697,665 B1 | | 2/2004 | Rava et al. |
| 2003/0191398 A1 | | 10/2003 | Motz et al. |

FOREIGN PATENT DOCUMENTS

| | | |
|---|---|---|
| WO | WO 93/03672 | 3/1993 |
| WO | WO 97/30338 | 8/1997 |
| WO | WO 02/077587 A2 | 10/2002 |
| WO | WO 2004/051242 A1 | 6/2004 |

OTHER PUBLICATIONS

Chen et al. Proceedings of the National Science Council, ROC Part B: Life Science.1996;20(4):123-130.*
Huang et al. Int. J. Cancer 2003;107:1047-1052.*
Hawi et al. Cancer Letters 1996;110:35-40.*
LeRoy et al. Canine prostate carcinomas express markers of uroghelial and prostatic differentiation. Vet. Pathol. (2004) 41:131-140.*
Crow et al. "The use of Raman spectroscopy to identify and grade prostatic adenocarcinoma in vitro", British Journal of Cancer, 2003, 89:106-108.*
Cussenot et al. "Noninvasive detection of genetic instability in cells from prostatic secrdtion as a marker of prostate cancer", European Journal of Internal Medicine, 2001, 12:17-19.*
Technology License Opportunity, "Hyperspectral Imaging for Cancer Detection", 2 pp., © 2004 Science Applications International Corporation.
Miseo, et al., "Developing a Chemical-Imaging Camera", The Industrial Physicist, Oct./Nov. 2003, 4 pp., © American Institute of Physics.

* cited by examiner

*Primary Examiner*—Karen Cochrane Carlson
*Assistant Examiner*—Bin Shen
(74) *Attorney, Agent, or Firm*—Morgan Lewis & Bockius

(57) ABSTRACT

Raman molecular imaging is used to differentiate between normal and diseased cells or tissue. For instance benign and malignant lesions of bladder and other tissues can be distinguished, including epithelial tissues such as lung, prostate, kidney, breast, and colon, and non-epithelial tissues, such as bone marrow and brain. Raman scattering data relevant to the disease state of cells or tissue can be combined with visual image data to produce hybrid images which depict both a magnified view of the cellular structures and information relating to the disease state of the individual cells in the field of view.

29 Claims, 21 Drawing Sheets

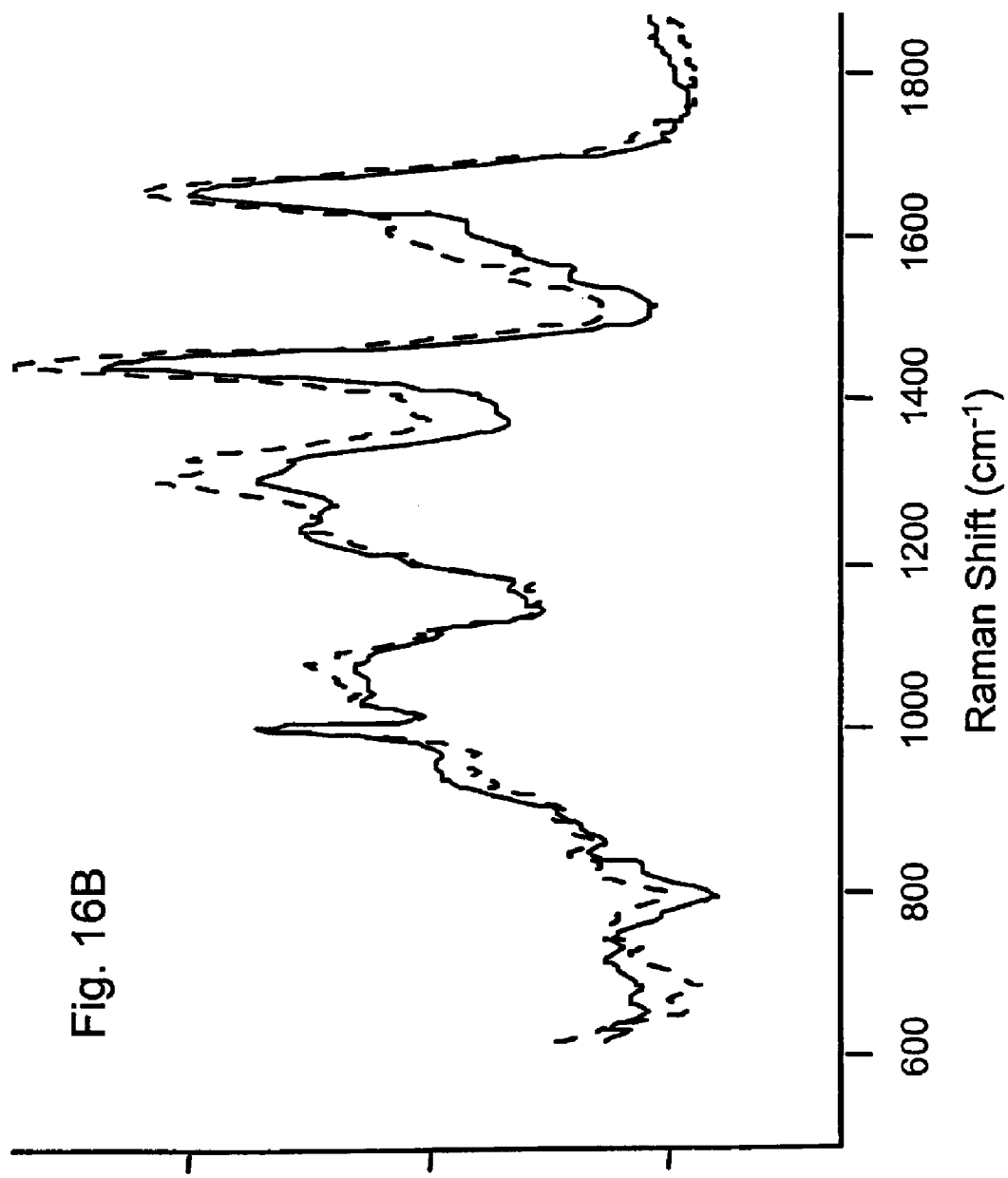

CYTOLOGICAL ANALYSIS BY RAMAN SPECTROSCOPIC IMAGING

CROSS-REFERENCES TO RELATED APPLICATIONS

This application is entitled to priority pursuant to 35 U.S.C. §119(e) to U.S. provisional patent application 60/568,357, which was filed on 5 May 2004.

BACKGROUND OF THE INVENTION

The invention relates generally to the field of mammalian cellular evaluation and to correlation of cellular physiological status and diagnosis of disease based on such evaluation.

Cells are a basic unit of life. The body of an individual human is made up of many trillions of cells, the overwhelming majority of which have differentiated to form tissues and cell populations of various discrete types. Cells in a healthy human often exhibit physical and biochemical features that are characteristic of the discrete cell or tissue type. Such features can include the size and shape of the cell, its motility, its mitotic status, its ability to interact with certain chemical or immunological reagents, and other observable characteristics.

The field of cytology involves microscopic analysis of cells to evaluate their structure, function, formation, origin, biochemical activities, pathology, and other characteristics. Known cytological techniques include fluorescent and visible light microscopic methods, alone or in conjunction with use of various staining reagents (e.g., hemotoxylin and eosin stains), labeling reagents (e.g., fluorophore-tagged antibodies), or combinations thereof.

Cytological analyses are most commonly performed on cells obtained from samples removed from the body of a mammal. In vivo cytological methods are often impractical owing, for example, to relative inaccessibility of the cells of interest and unsuitability of staining or labeling reagents for in vivo use. Cells are commonly obtained for cytological analysis by a variety of methods. By way of examples, cells can be obtained from a fluid that contacts a tissue of interest, such as a natural bodily fluid (e.g., blood, urine, lymph, sputum, peritoneal fluid, pleural fluid, or semen) or a fluid that is introduced into a body cavity and subsequently withdrawn (e.g., bronchial lavage, oral rinse, or peritoneal wash fluids). Cells can also be obtained by scraping or biopsying a tissue of interest. Cells obtained in one of these ways can be washed, mounted, stained, or otherwise treated to yield useful information prior to microscopic analysis.

Information obtained from cytological analysis can be used to characterize the status of one or more cells in a sample. By way of example, the size, shape, and approximate number and proportions of cell types observed in a blood sample can yield information about a variety of diseases and other physiological states of the patient from whom the blood was obtained. Information obtained from other cell types can also reveal the disease or other physiological status of particular cells and tissues in a patient.

Some diseases are caused by exogenous infectious or chemical agents which induce adverse cellular effects when the agents are contacted with cells in the body. Other diseases (e.g., diseases wholly or partially of hereditary origin, such as sickle cell anemia) can arise in the absence of harmful exogenous agents. Some disease states are readily discernable from cytological analysis, such as diseases in which cells assume a characteristic shape or reactivity and disease in which an infectious agent can be observed in an infected tissue. However, other disease states (including many physiological states which precede or indicate a predisposition to develop a disease state) cannot be readily detected by ordinary cytological methods.

A further shortcoming of many cytological methods is that, even when cytological identification of a disease state is possible, the time, expense, and expertise necessary to perform the cytological analysis can make it impractical or impossible to perform that analysis. Some cytological methods rely on qualitative judgments made by a cytologist, and those judgments can vary among cytologist, conferring subjectivity to the analysis. In many instances, objective analyses would be preferable.

The apparatus and methods described herein overcome many of the shortcoming of known cytological methods and complement many of the advantages of such methods.

Cancer Diagnosis

Cancer is the second leading cause of death in the United States, with more than 1.2 million new cancers being diagnosed annually. Cancer is significant, not only in terms of mortality and morbidity, but also in terms of the cost of treating advanced cancers and the reduced productivity and quality of life achieved by advanced cancer patients. Despite the common conception of cancers as incurable diseases, many cancers can be alleviated, slowed, or even cured if timely medical intervention can be administered. A widely recognized need exists for tools and methods for early detection of cancer.

Cancers arise by a variety of mechanisms, not all of which are well understood, from evidently normal tissue. Cancers, called tumors when they arise in the form of a solid mass, characteristically exhibit decontrolled growth and/or proliferation of cells. Cancer cells often exhibit other characteristic differences relative to the cell type from which they arise, including altered expression of cell surface, secreted, nuclear, and/or cytoplasmic proteins, altered antigenicity, altered lipid envelope (i.e., cell membrane) composition, altered production of nucleic acids, altered morphology, and other differences. Typically, cancers are diagnosed either by observation of tumor formation or by observation of one or more of these characteristic differences. Because cancers arise from cells of normal tissues, cancer cells usually initially closely resemble the cells of the original normal tissue, often making detection of cancer cells difficult until the cancer has progressed to a stage at which the differences between cancer cells and the corresponding original normal cells are more pronounced. Depending on the type of cancer, the cancer can have advanced to a relatively difficult-to-treat stage before it is easily detectable.

Early definitive detection and classification of cancer is often crucial to successful treatment. Diagnosis of cancer must precede cancer treatment. Included in the diagnosis of many cancers is determination of the type and grade of the cancer and the stage of its progression. This information can inform treatment selection, allowing use of milder treatments (i.e., having fewer undesirable side effects) for relatively early-stage, non- or slowly-spreading cancers and more aggressive treatment (i.e., having more undesirable side effects and/or a lower therapeutic index) of cancers that pose a greater risk to the patient's health.

When cancer is suspected, a physician will often have the tumor or a section of tissue having one or more abnormal characteristics removed or biopsied and sent for histopathological analyses. Typically, the time taken to prepare the specimen is on the order of one day or more. Communication of results from the pathologist to the physician and to the patient can further slow the diagnosis of the cancer and the onset of any indicated treatment. Patient anxiety can soar during the period between sample collection and diagnosis.

A recognized need exists to shorten the time required to analyze cells in order to determine whether or not the cells indicate the presence of cancer. Furthermore, it would be beneficial to reduce the number and/or volume of cells required for such determination, in order to minimize patient discomfort and improve patient acceptance of biopsy.

Although certain immunohistology techniques can be performed without the need for microscopic visualization of cells, almost all histopathological analysis of suspected cancer cells and tissues involves microscopic examination of the suspect cells or tissue. Optical microscopy techniques are most common, owing to their relative simplicity and the wealth of information that can be obtained by visual examination of cells and tissues.

A suspension of cells (e.g., cells in urine, blood, sputum, or a peritoneal or bronchial lavage) can be visually examined, with or without staining the suspended cells. A tissue biopsy obtained from a patient can be directly observed; stained and observed; embedded, sectioned, stained, and observed; or some combination of these.

In order to diagnose cancer, the cell or tissue preparation is analyzed by a trained pathologist who can differentiate between normal cells and malignant or benign cancer cells based on cellular morphology, tissue structure, staining characteristics, or some combination of these. Because of the tissue preparation required, this process is relatively slow. Moreover, the differentiation made by the pathologist is based on subtle morphological and other differences among normal, malignant, and benign cells, and such subtle differences can be difficult or time-consuming to detect, even for highly experienced pathologists. Such differences are even more difficult for relatively inexperienced pathologists to detect.

Clinicians typically classify cancer lesions by assigning a grade and a stage to the lesion after superficial examination of the lesion and microscopic analysis of a biopsy taken from the lesioned tissue or organ. Grading and staging of cancers is performed by analyzing the bodily location, morphology, and extent of tissue invasion of cancer cells. The definitions of the various grades and stages of tumors vary with the type of cancer.

Grade describes the aggressiveness of the tumor cells, referring to their growth rate and likelihood of invading surrounding or distant (i.e., by metastasis) tissues. Grading is determined by microscopic analysis of tumor cells, whereby a pathologist examines how differentiated the tumor cells are from normal (non-tumorous) tissue of the same type. Tumors that resemble the corresponding normal tissue (i.e., low grade tumors) tend to grow and spread relatively slowly. In contrast, high grade tumors (i.e., those which do not resemble the corresponding normal tissue) tend to grow and spread more quickly. Patient survival is also correlated with cancer grade, higher grade corresponding to lower likelihood of survival. There are multiple systems for describing the grade of a tumors. Common systems rely on a three- or four-point grading system, the higher numbers referring to higher cancer grade. The grading system used is indicated in the grade designation, for example "I/III" referring to grade I on a three point scale and "II/IV" referring to grade II on a four-point scale. Stage describes the anatomical progression of a tumor. A variety of staging systems have been described for various tumor types.

The apparatus and methods described herein can be used to enhance or replace current cancer diagnostic methods.

Sickle Cell Trait

Red blood cells (RBCs) transport oxygen through the bloodstream from the lungs to other tissues in the body. The oxygen is bound to a protein called hemoglobin, which normally exists in the form of a tetramer of protein subunits. The bodies of some individuals are capable of making both normal and altered hemoglobin protein subunits. The altered hemoglobin subunits confer to hemoglobin that trait that, under certain circumstances, hemoglobin can polymerize. When hemoglobin polymerizes, the normal disk shape of RBCs is distorted such that RBCs take on a curved, elongated ("sickle") shape. Sickle-shaped RBCs are not able to pass through narrow blood vessels as easily as normal RBCs. As a result, sickle RBCs can obstruct blood flow, causing damage to blood vessels and tissues that depend on those vessels for oxygen and nourishment.

The adverse effects of sickle RBCs are often not noticed until significant tissue damage has been done. Furthermore, individuals who make both normal and altered hemoglobin are often not identified, because they suffer few or no adverse effects. Children of two individuals, each of whom makes both normal and altered hemoglobin are at increased risk for sickle cell diseases such as sickle cell anemia, thalassemia, stroke, and damage to multiple organs. It is useful to identify individuals who make both normal and altered hemoglobin so that those individuals can make informed decisions regarding childbearing.

Currently, electrophoretic techniques are used to identify individuals who make altered forms of hemoglobin. Nucleic acid-based tests can also be used to diagnose individuals. However, once an individual has been diagnosed with sickle cell disease or as a carrier of the sickle cell trait, medical interventions are limited. Administration of hydroxyurea, for example, can enhance production of a fetal form of hemoglobin that inhibits RBC sickling. A method of identifying abnormal RBCs prior to sickling can identify individuals at risk for developing sickle cell disease or passing the sickle cell trait. Cytological methods for identifying RBCs expressing altered forms of hemoglobin can also permit treatment and/or manipulation of individual RBCs. Apparatus and methods of using them for these purposes are disclosed herein.

Heart Diseases

The heart pumps blood throughout the body and is responsible for providing oxygen and nourishment to substantially all tissues. Cardiac muscle cells of the heart can be adversely affected by a variety of disease states including, for example angina; coronary artery disease and atherosclerosis; inflammatory diseases; neoplasia; viral, bacterial, protozoan, and parasitic infections; cardiac insufficiency and failure; inherited myopathies; and myocardial deterioration attributable to mineral deficiency. Because cardiac muscle tissue is not easily accessible, the effects of these disease states on cardiac muscle tissue cannot be easily observed. For this reason, diagnostic methods which rely on observations of cardiac muscle tissue have not been widely used.

Apparatus and methods useful for direct analysis of cardiac muscle tissue would hasten and simplify diagnosis of heart disease states and permit earlier and more efficacious treatment. Apparatus and methods of using them for these purposes are disclosed herein.

Raman Spectroscopy

Raman spectroscopy provides information about the vibrational state of molecules. Many molecules have atomic bonds capable of existing in a number of vibrational states. Such molecules are able to absorb incident radiation that matches a transition between two of its allowed vibrational states and to subsequently emit the radiation. Most often, absorbed radiation is re-radiated at the same wavelength, a process designated Rayleigh or elastic scattering. In some instances, the re-radiated radiation can contain slightly more or slightly less energy than the absorbed radiation (depending on the allowable vibrational states and the initial and final vibrational states of the molecule). The result of the energy difference between the incident and re-radiated radiation is manifested as a shift in the wavelength between the incident and re-radiated radiation, and the degree of difference is designated the Raman shift (RS), measured in units of wavenumber (inverse length). If the incident light is substantially monochromatic (single wavelength) as it is when using a laser source, the scattered light which differs in wavelength from the incident light can be more easily distinguished from the Rayleigh scattered light.

Because Raman spectroscopy is based on irradiation of a sample and detection of scattered radiation, it can be employed non-invasively or to analyze biological samples in situ. Thus, little or no sample preparation is required. In addition, water exhibits very little Raman scattering, and Raman spectroscopy techniques can be readily performed in aqueous environments.

Others have performed Raman spectroscopic analysis of biological tissues. Descriptions of such analyses can be found in the following publications: Petrich, 2001, Appl. Spectrosc. Rev. 36:181; Naumann, 2001, Appl. Spectrosc. Rev. 36:239; Manoharan et al., 1998, Photochem. Photobiol. 67:15; Frank et al., 1995, Anal. Chem. 67:777; Redd et al., 1993, Appl. Spectrosc. 47:787; Haka et al., 2002, Cancer Res. 62:5375; Utzinger et al., 2001, Appl. Spectrosc. 55:955; Liu et al., 1992, Lasers Life Sci. 4:257; Frank et al., 1994, Anal. Chem. 66:319; Bakker-Schut et al., 2002, J. Raman Spectrosc. 33:580; Notingher et al., 2003, Biopolymers (Biospectroscopy) 72:230-240; international patent application publication no. WO 93/03672; international patent application publication no. WO 97/30338; U.S. Pat. No. 6,697,665; U.S. Pat. No. 6,174,291; U.S. Pat. No. 6,095,982; U.S. Pat. No. 5,991,653; and U.S. patent application publication no. 2003/0191398. These investigators used traditional Raman sampling approaches in which tissues are analyzed by collecting a Raman spectrum from a narrowly focused point in a sample.

Still other investigators (e.g., international publication no. WO 2004/051242; Krafft et al., 2003, Vibr. Spectrosc. 32:75-83; Kneipp et al., 2003, Vibr. Spectrosc. 32:67-74) used a Raman mapping approach wherein Raman spectra were obtained using a scanning sample holder or light source to generate a spectroscopic map of the sample. To implement this scanning strategy, there is an inherent trade off between acquisition time and the spatial resolution of the spectroscopic map. Each full spectrum takes a certain time to collect. The more spectra collected per unit area of a sample, the higher the apparent resolution of the spectroscopic map, but the longer the data acquisition takes. Performing single point measurements on a grid over a field of view will also introduce sampling errors which makes a high definition image difficult or impossible to construct. Moreover, the serial nature of the spectral sampling (i.e., the first spectrum in a map is taken at a different time than the last spectrum in a map) decreases the internal consistency of a given dataset, making the powerful tools of chemometric analysis more difficult to apply.

An apparatus for Raman Chemical Imaging (RCI) has been described by Treado in U.S. Pat. No. 6,002,476, and in co-pending U.S. Non-Provisional application Ser. No. 09/619, 371, which are incorporated herein by reference. Treado disclosed that Raman molecular imaging can be used to distinguish breast cancer tissue from normal breast tissue, but did not disclose how or whether any similar method might be applicable to diagnosis, grading, or staging of bladder cancers or other cancer diagnostic methods and protocols.

The invention alleviates or overcomes the limitations of prior art tools and methods for cancer diagnosis, grading, and staging and permits diagnosis of a variety of disease states.

BRIEF SUMMARY OF THE INVENTION

The invention relates to a method of assessing the disease state of mammalian cells, such as human red blood cells (RBCs) or human cardiac muscle cells. The method comprises irradiating one or more cells with substantially monochromatic light, such as laser light having a wavelength in the range from 220 to 695 nanometers. Raman scattered light emitted by the cells is assessed, for example at Raman shift (RS) values in the ranges from about 280 to 1800 $cm^{-1}$ and from 2750 to 3200 $cm^{-1}$. The intensity of the Raman scattered light emitted by the cells is compared with a reference value, multiple reference values, or a reference spectrum that corresponds to the intensity of Raman scattered light emitted by a reference cell of the same type. A difference between the intensity of the Raman scattered light emitted by the analyzed cells and the reference is indicative of the disease state of the cells (e.g., indicative of the degree to which RBCs express the aberrant form of hemoglobin associated with the sickle cell disease). The reference value can be a value obtained by a separate measurement performed at substantially the same time as the sample measurement, or a value stored or input into an electronic memory, for example. Preferably, the disease state of the reference cell is known.

In one embodiment, it has been discovered that sickled red blood cells (RBCs) exhibit Raman spectral characteristics that can be distinguished from those of normal RBCs. Distinctions can be observed among spectral characteristics of Raman shifted light having RS values in the ranges from about 500 to 1800 $cm^{-1}$ (e.g., in the range from about 650 to 1650 $cm^{-1}$). These distinguishing characteristics include Raman spectral characteristics that are detected within the first 100 milliseconds after illuminating an RBC for Raman analysis, such as a Raman peak shift from RS=1086 $cm^{-1}$ to RS=1070 $cm^{-1}$, a Raman peak shift from RS=671 $cm^{-1}$ to RS=666 $cm^{-1}$, and a Raman peak shift and peak broadening from RS=996 $cm^{-1}$ to RS=991 $cm^{-1}$. The Raman spectral characteristics by which sickled and normal RBCs can be distinguished also include Raman spectral characteristics that are detected following prolonged (e.g., >1 second) illumination an RBC for Raman analysis, such as differences in peak heights at RS values of about 1366 $cm^{-1}$ and 1389 $cm^{-1}$. These differences, and the differences between Raman spectra upon initial and prolonged illumination can be observed dynamically. By way of example, under illumination conditions described herein, RBCs generally exhibited stable Raman spectral characteristics after about 1 second of illumination, with dynamic spectral changes occurring on the time scale of tens of milliseconds after illumination began.

In another embodiment, it has been discovered that information indicative of the disease state (e.g., ischemic status or likelihood of experiencing idiopathic heart failure) of human cardiac cells and tissues can be obtained from Raman spectral data, such as spectral characteristics in Raman shifted light having RS values in the ranges from about 500 to 1800 $cm^{-1}$ (e.g., in the range from about 750 to 1650 $cm^{-1}$). By way of example, characteristic Raman spectral features of connective tissue fibers of patients afflicted with ischemic and idiopathic heart failure are observable at RS values of about 747, 1080, 1125, 1309, 1358, 1584, and 1165 cm$^{-1}$. Similarly, characteristic Raman spectral features of cardiac muscle cell bundles of patients afflicted with ischemic and idiopathic heart failure are observable at RS values of about 1080, 1584, and 1665 cm$^{-1}$.

In still another embodiment, it has been discovered that information indicative of cancerous state of bladder cells and other cancer cells (including epithelial and other cancers) can be obtained from Raman shifted light having RS values in the ranges from 1000 to 1650 cm$^{-1}$ and from 2750 to 3200 cm$^{-1}$. Particularly informative values include RS values in the range from 1500 to 1650 cm$^{-1}$. The RS value of about 1584 cm$^{-1}$ is considered particularly informative for bladder cancer and other cancers. Other preferred RS values include RS values of about 1000, 1100, 1250, 1370, and 2900 cm$^{-1}$.

It has also been discovered that information indicative of cancerous state of prostate cells can be obtained from Raman shifted light having RS values in the ranges from 1000 to 1605 cm$^{-1}$. Particularly informative values include RS values of about 1080, 1300, and 1600 cm$^{-1}$.

A variety of sources of substantially monochromatic light can be used in the apparatus and methods described herein, such as lasers (e.g., a diode pumped solid state laser). The illumination wavelength should be not greater than about 695 nanometers, and is preferably not less than about 280 nanometers. For example, a suitable laser can produce substantially monochromatic light having a wavelength of about 532 nanometers. Preferably, the bandwidth (full height at half maximum) of the substantially monochromatic light is not greater than about 0.25 nanometer.

The methods described herein can be used to assess Raman scattering by cells either in vitro or in vivo. When in vitro analysis is performed, the cells are preferably substantially separated from debris or other potentially interfering substances prior to assessing Raman scattered light emitted by the cells.

Instead of simply comparing a characteristic (e.g., intensity) of Raman scattered light at a single RS value, the analysis can be performed by assessing Raman scattered light emitted by the cells of interest at two sampled RS values in the range, and comparing the ratio of intensities of the Raman scattered light emitted by the cells at the sampled RS values with a reference ratio value corresponding to the ratio of intensities of Raman scattered light emitted by a reference cell at the sampled RS values. Of course, Raman scattering intensities at three or more RS values can be compared. In addition, the shape and relative intensities of Raman scattering over a spectrum of RS values can be compared.

By making a plurality of Raman light scattering assessments of a sample (e.g., using an array of detectors in parallel), a map or image of Raman scattering information corresponding to the sample can be made. This map or image can be used by itself or combined with a visual image of the cell, optionally including its surroundings (e.g., other cells, tissues, or extracellular matrix). The Raman molecular image so produced can be used to characterize occurrence of diseased cells in a sample, such as occurrence of cancerous cells in a tissue sample.

The disease status of a cell can be assessed directly (e.g., by detecting expression of a disease marker by the cell, such as an altered form of hemoglobin). The disease status can also be assessed by examining Raman spectral features characteristic of diseased status, regardless of whether the molecules giving rise to those features are known. Disease status can also be determined by combining information obtained from Raman spectral features and from other spectroscopic properties (e.g., visibly discernable properties such as size and shape and non-Raman spectral properties such s absorbance or fluorescent emissions). In addition to assessing disease states, these data can be correlated with other cellular states, such as the metabolic state of the cell, the inflammatory status of a tissue, or the autoimmune status of a cell or tissue (e.g., whether an autoimmune reaction is occurring in a tissue).

BRIEF SUMMARY OF THE SEVERAL VIEWS OF THE DRAWINGS

FIG. 4 comprises FIGS. 4A, 4B, 4C, and 4D.

FIG. 16, comprising FIGS. 16A and 16B, is a comparison of averaged Raman scattering intensities between prostate tissue samples obtained from 64 patients diagnosed with prostate cancer (solid line) and prostate tissue samples obtained from 32 patients whose prostate tissue was determined to be benign (dashed line). FIG. 16B is a magnified portion of the graph in FIG. 16A.

DETAILED DESCRIPTION OF THE INVENTION

Figure 1:
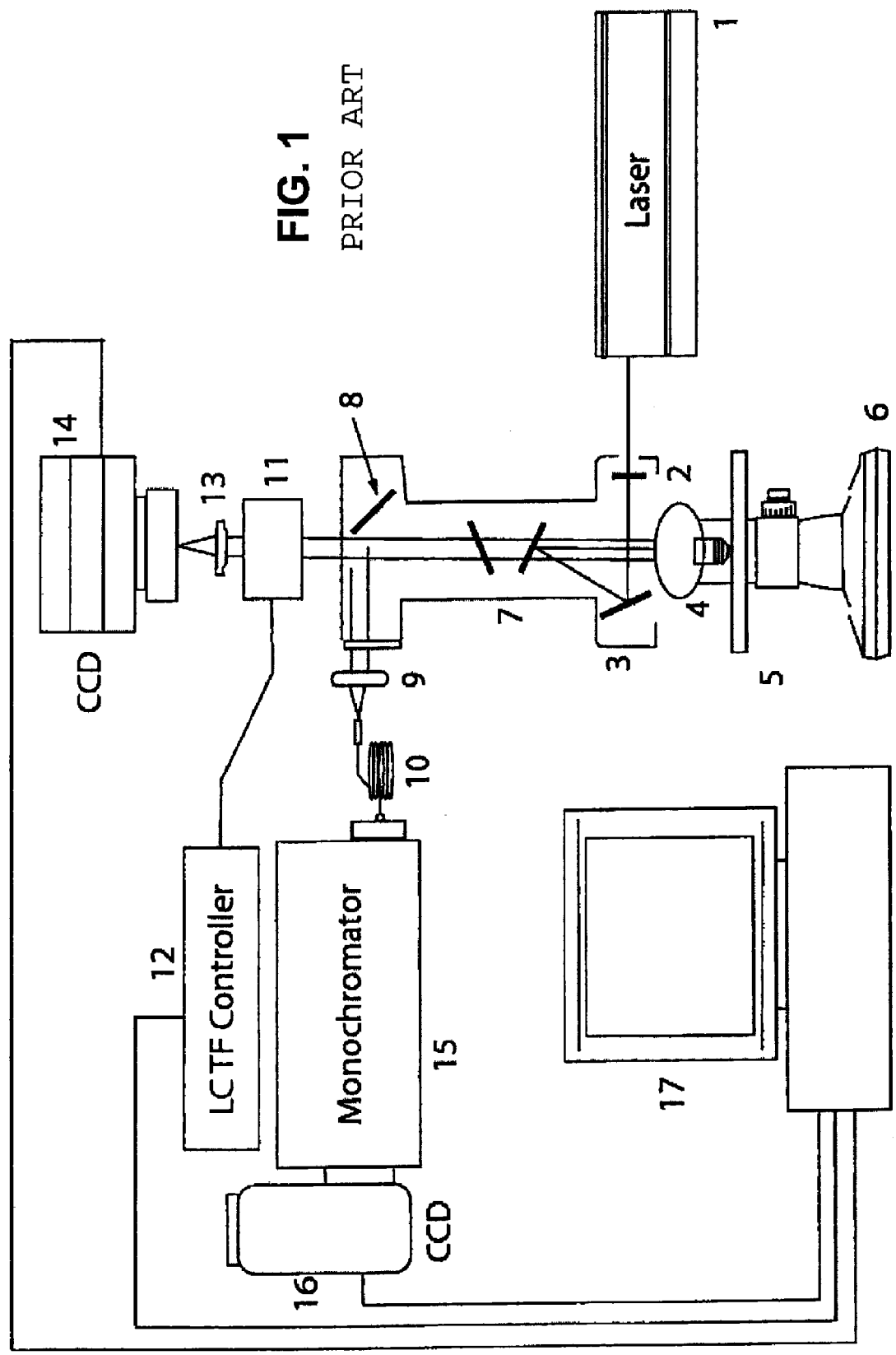
FIG. 1 is a schematic diagram of an embodiment of the Raman chemical imaging system more fully described in U.S. Pat. No. 6,002,476.

The invention relates to methods of assessing the disease state of a mammalian cell using a Raman spectroscopic approach. The methods are useful for assessing cells known or suspected of being cancerous, for purposes of cancer diagnosis, grading, and/or staging. The methods are useful for cancer assessment of cells of at least bladder, prostate, lung, colon, kidney, breast, and brain. The methods are also useful for assessing disease states not necessarily associated with cancer, such as infection, inflammation, autoimmune attack, cardiac dysfunction, and hemoglobinopathies. The methods can be used to detect cells affected by congenital defects, such as sickling of red blood cells (RBCs) and cardiac muscle and connective tissues affected by a hereditary cardiomyopathy.

Raman spectroscopic data will suffice in some instances to identify occurrence of a disease state. However, it is often preferable to assess the disease state present at discrete locations within a cell sample (e.g., to assess the disease state of individual cells), such as when the cells are assessed in vivo. In such instances, Raman spectral data is simultaneously collected at a plurality of discrete locations within the sample, and the Raman data so generated can be assembled to form an image of the sample that reflects the Raman spectral properties of the discrete portions of the sample. Raman spectral data can be combined with other spectroscopic information, such as a visible light microscopic image of the sample, to generate data representations (e.g., images) of the sample that are more informative than either the Raman data or the other spectroscopic data alone.

The methods described herein involve irradiating a sample including one or more mammalian cells with substantially monochromatic light and assessing Raman light scattering from the cell(s), preferably at many points on the cells in the sample or from entire areas of the sample (e.g., from an area that includes multiple cells). The intensity of Raman light scattering at one or more Raman shift values can be assessed by itself. However, a more information-rich image can be made by combining the Raman scattering data with visual microscopy data to make a hybrid image. In such an image, visual clues to the disease and/or metabolic state of the cell(s) in the sample can be derived from morphological and structural information derived from the visual microscopic image data, from the Raman scattering data, and from the superposition and/or integration of the two data sets.

The methods described herein allow quantitative evaluation of cell and tissue samples with little or no necessary sample preparation. Because the methods require relatively little cellular material, they can be performed in a non-invasive or minimally invasive manner. The methods are also suitable for in vivo or in situ use, such as with a probe inserted into a tissue or body cavity.

Definitions

As used herein, each of the following terms has the meaning associated with it in this section.

"Bandwidth" means the range of wavelengths in a beam of radiation, as assessed using the full width at half maximum method.

"Bandpass" of a detector or other system means the range of wavelengths that the detector or system passes through itself, as assessed using the full width at half maximum intensity method.

The "full width at half maximum" ("FWHM") method is a way of characterizing radiation including a range of wavelengths by identifying the range of contiguous wavelengths that over which the magnitude of a property (e.g., intensity or detection capacity) is equal to at least half the maximum magnitude of that property in the radiation at a single wavelength.

"Spectral resolution" means the ability of a radiation detection system to resolve two spectral peaks.

DETAILED DESCRIPTION

Raman Spectroscopic Analysis for Assessment of Disease State

The invention is based, in part, on the discovery that diseased cells, when irradiated with radiation having a wavelength in the range from 220 to 695 nanometers (the wavelength preferably being greater than 280 nanometers, such as radiation having a wavelength in the range from 500 to 695 nanometers), exhibit Raman scattering of the applied radiation, and that the wavelength of the Raman scattered light emitted by those irradiated cells is shifted by amounts characteristic of the diseased cells. That is, cells which are diseased exhibit a different Raman spectrum than do cells of the same type that are not diseased. The differences in the spectra can include, for example, changes in the intensity of Raman scattered light at certain RS values, changes in the shape of the Raman scattering spectrum over a range of RS values, changes in the ratio of the intensity of Raman scattered light at two RS values, and combinations of these. These differences can be used to assess the disease status of a mammalian cell, the tissue from which the cell is obtained, or the tissue in which the cell is located.

In order to detect Raman scattered light and to accurately determine the Raman shift of that light, the cells should be irradiated with substantially monochromatic light, such as light having a bandwidth not greater than about 1.3 nanometers, and preferably not greater than 1.0, 0.50, or 0.25 nanometer. Suitable sources include various lasers and polychromatic light source-monochromator combinations. It is recognized that the bandwidth of the irradiating light, the resolution of the wavelength resolving element(s), and the spectral range of the detector determine how well a spectral feature can be observed, detected, or distinguished from other spectral features. The combined properties of these elements (i.e., the light source, the filter, grating, or other mechanism used to distinguish Raman scattered light by wavelength; and the detector) define the spectral resolution of the Raman signal detection system. The known relationships of these elements enable the skilled artisan to select appropriate components in readily calculable ways. Limitations in spectral resolution of the system (e.g., limitations relating to the bandwidth of irradiating light) can limit the ability to resolve, detect, or distinguish spectral features. The skilled artisan understands that and how the separation and shape of Raman scattering signals can determine the acceptable limits of spectral resolution for the system for any of the Raman spectral features described herein.

In general, the wavelength and bandwidth of light used to illuminate the sample is not critical, so long as the other optical elements of the system operate in the same spectral range as the light source. For a diffraction grating, the spectral resolution is defined as the ratio between the wavelength of interest and the separation, in the same units as the wavelength, required to distinguish a second wavelength. By way of example, the apparatus described in the examples herein can distinguish a Raman shift band at 1584 cm$^{-1}$ from a separate peak that differs by about 12 cm$^{-1}$. Therefore, the Raman peak resolving power is 1584/12, or about 132, for the apparatus described in the examples. With a broader source (or a source filter enabling passage of light exhibiting an intensity profile characterized by a greater full width half maximum), greater peak separation would be required, because the Raman peaks would be more blurred on account of the greater variety of irradiating wavelengths that are shifted. Such a system would have a lower Raman peak resolving power.

By way of example, a suitable Raman peak resolving power can be determined as follows. If the lower limit of performance for a peak of interest at 1584 cm$^{-1}$ is distinguishing a peak at 1605 cm$^{-1}$, then this represents a separation of 66 wavenumbers. This indicates that the lower limit of Raman peak resolving power is about 1584/66=24 for these peaks. Similar calculations can be performed to determine the minimum resolving power required for distinguishing other Raman peaks described herein.

The source of substantially monochromatic light is preferably a laser source, such as a diode pumped solid state laser (e.g., a Nd:YAG or Nd:YVO$_4$ laser) capable of delivering monochromatic light at a wavelength of 532 nanometers. Other lasers useful for providing substantially monochromatic light having a wavelength in the range from about 280 to 695 nanometers include HeNe (which can be used to supply irradiation at any of several spectral lines, at about 543, 594, 612, and 633 nanometers), argon ion (532 nanometers), argon gas (360 nanometers), HeCd (442 nanometers), krypton (417 nanometers), and GaN (408 nanometers, although doped GaN lasers can provide 350 nanometers). Other lasers can be used as well, such as red diode lasers (70-785 nanometers) and eximer lasers (20-300 nanometers). Use of ultraviolet irradiation can permit use of resonance Raman techniques, which can yield more intense signals and simplified spectral peaks. However, lasers capable of ultraviolet irradiation tend to be very costly and complex to use, limiting their desirability.

Because Raman scattering peaks are independent of the wavelength of the illumination source (i.e., the RS value does not depend on the incident wavelength), the wavelength of light used to irradiate the cells is not critical. However, the illumination wavelength influences the intensity of the Raman peaks and the fluorescent background signals detected. Others have believed that irradiating cells with light having a wavelength less than those commonly used (i.e., light having a wavelength greater than about 700 nanometers is commonly used) would harm cells in the illuminated sample, owing to energy absorption by the cells.

As described herein, it has been discovered that wavelengths at least as low as about 500 nanometers (e.g., from 350 to 695 nanometers), and likely as low as 280 nanometers or even 220 nanometers, can be used without causing significant cell damage, especially if wide-field illumination techniques are employed and the intensity of the illuminating radiation is carefully controlled. Because the intensity of scattered light is known to be dependent on the fourth power of the frequency (i.e., inverse wavelength) of the irradiating light, and only proportional to the intensity of the irradiating light, lowering the wavelength of the irradiating light has the effect of increasing scattering signal output. Thus, a Raman scattering signal of equal intensity can be obtained by irradiating a sample with light having a higher wavelength and by irradiating the sample with a lower (irradiation) intensity of light having a shorter wavelength. Even under constant illumination, cells can survive irradiation with light having a wavelength as short as 500 nanometers if the intensity of the irradiating light is controlled. Irradiation using even shorter wavelengths can be performed without harming the illuminated cells if intermittent or very short duration irradiation methods are employed. Irradiating cells with sub-700 nanometer wavelength light significantly boosts the Raman scattering signal obtained from the cells, leading to greater intensity and resolution of the Raman spectra of the cells and permitting more sensitive assessment of the disease state of the cells than was possible using previous methods.

An appropriate irradiation wavelength can be selected based on the detection capabilities of the detector used for assessing scattered radiation. Most detectors are capable of sensing radiation only in a certain range of frequencies, and some detectors detect frequencies in certain ranges less well than they do frequencies outside those ranges. In view of the Raman shift values that can be expected from tumor tissue samples, as disclosed herein, many combinations of light sources and detectors will be appropriate for use in the systems and methods described herein. By way of example, front- and back-illuminated silicon charge coupled device (CCD) detectors are useful for detecting Raman scattered light in combination with irradiation wavelengths described herein.

A sample including one or more cells can be irradiated by the light source in a diffuse or focused way, using ordinary optics. In one embodiment, light from the source is focused on a portion of a single cell of the sample and Raman scattering from that portion is assessed. A limitation of this approach is that the power input on the illuminated area must not be so great that the cell is harmed or significantly altered, at least prior to assessment of Raman scattering. Preferably, the amount of energy transferred to the cell during illumination is not sufficient to alter the morphology, Raman spectral characteristics, or other characteristics of the cell relevant for assessment of its state.

In another embodiment, the light used to irradiate the cells is focused on a larger (i.e., whole cell or multi-cell) portion of the sample or the entire sample. Use of such wide-field illumination can diffuse the irradiation power density across the sample, reducing the rate of energy transfer to the cells therein and protecting their function and viability. Wide-field illumination allows the acquisition of data and assessment of Raman scattering across the illuminated field or, if coupled with wide-field parallel detectors, can permit rapid Raman scattering analysis across all or part of the illuminated field. This facilitates presentation of Raman scattering data in the form of an image of all or part of the illuminated field, either alone or in combination with data obtained from the field using other spectroscopic methods. In contrast, scanning spot methods to detect Raman scattering require high laser power densities focused into a small region.

The maximum useful power density of irradiation depends on the need for post-Raman scattering assessment of the cells and the anticipated duration of irradiation. The duration and power density of irradiation must not combine to render the irradiated cells unsuitable for any desired post-assessment use. For example, when cells are irradiated in vivo, it is important that the irradiation not significantly impair the viability or biological function of the cells. In vivo irradiation should also not significantly alter the chemical signature, composition, or biological integrity of the irradiated cells and tissues. The skilled artisan is able to select irradiation criteria sufficient to avoid these effects. When prolonged irradiation of the sample is anticipated (e.g., an irradiation period of minutes or hours, corresponding to a reasonable estimate of the duration of pathologist examination), the power density of illumination should be sufficiently low that the sample is not appreciably altered during the period of illumination.

If desired, the intensity of irradiation can be deliberately selected to harm or kill illuminated cells. It can be desirable to kill diseased cells that are detected in vivo. By way of example, if a portion of the bladder epithelium of a patient is imaged using the methods described herein and portions of the epithelium are identified which harbor cancerous cells, those portions can be subjected to intense or prolonged irradiation in order to kill the cancerous cells. Alternatively, the Raman imaging methods described herein can be used to identify undesirable cells in vivo, and those undesirable cells can be ablated using a separate system which optionally employs the optics used for Raman imaging (or separate optics). Owing to the high resolution of the Raman scattering methods described herein, small tissue lesions can be precisely killed, even if those lesions are surrounded by or interspersed with regions of healthy tissue. Thus, for example, these methods can be used to direct destruction of cancerous cells in an epithelium. Similarly, the methods can be used to identify portions of an in vitro sample that contain diseased cells, so that those portions can be selected, discarded, or treated in desired ways.

Imagographic analysis of Raman scattering on a cellular scale can be performed using known microscopic imaging components. High magnification lenses are preferred, owing to their higher light collection relative to low magnification lenses. The numerical aperture of the lens determines the acceptance angle of light into the lens, so the amount of light collected by the lens varies with the square of the numerical aperture. By way of example, a 100× objective lens will typically have a numerical aperture value of about 0.9, and most 20× objective lenses will have a numerical aperture of about 0.4. Thus, the amount of light collected by the 100× lens will be about five times greater than the amount of light collected by the 20× lens. In view of the fact that Raman scattered light can have a relatively low magnitude, selection of a high magnification lens can improve low level signal detection.

Raman scattered radiation can be assessed on a cell-by-cell basis, by comparing regions of a single cell, or by comparing regions that contain multiple cells, for example. The cell or cells from which Raman scattering is assessed can be single cells, multiple cells of substantially a single type, or multiple cells of mixed types. When cells of mixed types are assessed, the Raman spectral data can be assessed on a averaged (over all cells present) basis or by extracting spectral information to one or more cell types from the raw data. Spectral unmixing techniques for extracting spectral information from data obtained from complex systems are known. Suitable spectral unmixing techniques are described, for example, in co-pending U.S. patent application Ser. No. 10/812,233, filed 29 Mar. 2004. The suitability of averaged spectral data depends on the extent to which non-diseased cells present in a mixture are known or expected to obscure a Raman spectral characteristic of a normal or diseased cell of a desired type in the mixture. For example, in a mixture of cell types, if a diseased cell of the type one wishes to assess exhibits a characteristic Raman spectral feature (e.g., a peak at a particular RS value) that is distinguishable from the Raman signals exhibited by all other cell types in the mixture, then the diseased cells can be detected without resolving the spectra of the cell types in the mixture.

Raman spectral data can be collected in the form of an two- or three-dimensional image that maps Raman scattering with position in a sample, as described herein. Such imaging methods can be used to produce Raman images (displayed alone or in combination with other spectroscopic data such as a visible light reflectance microscopic image) of individual cells, subcellular regions thereof, or intercellular regions (e.g., extracellular matrix). The cells can be isolated cells, such as individual blood cells or cells of a solid tissue that have been separated from other cells of the tissue. When the imaged cells are ordered (e.g., cells aligned by shape or cells arrayed in a solid tissue matrix), Raman spectral data can be collected at various positions relative to the cells and the polarization characteristics of the Raman scattered light can be assessed, each in order to derive position- and orientation-related information about the Raman scattering entities of the cells.

Assessment of Raman scattered light can be measured using any known detector appropriate for sensing radiation of the expected wavelength (generally about 5 to 200 nanometers greater than the wavelength of the irradiating radiation). In view of the relatively low intensities of many Raman scattered light signals, a highly sensitive detector may be preferred or required, such as one or more cooled charge-coupled device (CCD) detectors. For parallel operation, CCD detectors having multiple pixels corresponding to discrete locations in the field of illumination can be used to enable simultaneous capture of spectroscopic data at all pixel locations in the CCD detector.

Raman scattered light can be assessed at individual points in a sample, or an optical image of the Raman scattered light can be generated using conventional optics. The Raman data or image can be visually displayed alone or in combination with (e.g., superimposed upon) a microscopic image of the sample. Conventional methods of highlighting selected Raman data (e.g., by color coding or modulating the intensity of Raman scattered light) can be used to differentiate Raman signals arising from various parts of the sample. By way of example, the intensity of Raman scattered light having a Raman shift of 1584 cm$^{-1}$ can be displayed in varying shades or intensity of green color, superimposed on a brightfield optical microscopic image of the sample. In this way, Raman scattering can be correlated with microscopic landmarks in the sample.

If the cells are irradiated using light having a wavelength in the range from about 500 to 700 nanometers, then an RS value in the range 1000 to 1605 cm$^{-1}$ can be assessed using a detector capable of detecting radiation having a wavelength of about 550 to 785 nanometers, and an RS value in the range 2750-3200 cm$^{-1}$ can be assessed using a detector capable of detecting radiation having a wavelength of about 650 to 890 nanometers. Selection of an appropriate detector can be routinely performed by a skilled artisan in view of the irradiation light and the anticipated Raman shifts.

Raman scattering intensity values assessed at one or more RS values can be correlated with the disease state of the corresponding cell(s) by observing the existence (or non-existence) of increased RS intensity relative to a normal (i.e., non-diseased) cell or to a cell exhibiting a lower grade or severity of the disease. This assessment can be performed using raw intensity values, by comparing intensities at different parts of a sample (e.g., portions that exhibit distinct morphological appearances), by comparing intensity at multiple RS values, by combining analysis of an RS value with light microscopy information, by comparing the shape of Raman spectra assessed over a defined range, or by other methods apparent to one skilled in Raman spectroscopy, pathology, visible light microscopy, or some combination of these disciplines.

The ratio of Raman scattering intensities at two RS values can vary at different irradiation wavelengths, but will normally exhibit similar trends. This variation is attributable to the nature of Raman scattering. Raman scattering at a particular RS value depends on both the electronic and vibrational structure of the illuminated molecule. Ordinarily, the electronic state of the molecule does not affect Raman scattering, and electronic and vibrational structures are often considered independent of one another to simplify understanding. Sometimes, however, the energy of illuminating radiation can be used to shift the electronic state of the illuminated molecule, and the transition of the molecule between electronic states resonantly enhances vibration of the molecule. The result of these processes is a very significant (e.g., 100- to 1000-fold) increase in the intensity of the scattered radiation. This enhanced scattering intensity is commonly called resonance Raman scattering and can greatly simplify signal detection, especially in noisy backgrounds. By varying the wavelength of light used to illuminate a cell, resonance Raman effects can be avoided or taken advantage of (e.g., depending on whether the resonating molecule corresponds to an RS value that is informative regarding the disease state of a cell or not).

The methods described herein can be used by assessing the intensity of light scattered from a portion of the sample and subtracting out the intensity of light scattered from a different, reference portion of the sample that is known or believed to correspond to normal (i.e., non-diseased) tissue or from a separate sample of non-diseased cells of the same type. For example, RS data from different cells or from different areas of a single bladder tissue sample (or urine cytology slide) can be compared. A difference of scattered light intensity between the analyzed and reference portions of the sample indicates a difference in cancerous state of bladder cells.

Cells include many chemical species, and irradiation of cells can result in Raman scattering at a variety of wavelengths. In order to determine the intensity of Raman scattered light at various RS values, scattered light corresponding to other RS values must be filtered or directed away from the detector. A filter, filter combination, or filter mechanism can be interposed between the irradiated sample and the detector to accomplish this. The system (i.e., taking into account the bandwidth of the irradiating radiation and the bandpass of any filter or detector) should exhibit relatively narrow spectral resolution (preferably not greater than about 1.3 nanometers, and more preferably not greater than about 1.0, 0.5, or 0.25 nanometers) in order to allow accurate definition and calculation of RS values for closely spaced Raman peaks. If selectable or tunable filters are employed, then they preferably provide high out-of-RS band rejection, broad free spectral range, high peak transmittance, and highly reproducible filter characteristics. A tunable filter should exhibit a spectral resolving power sufficient for Raman spectrum generation (e.g., a spectral resolving power preferably not less than about 12-24 cm$^{-1}$ ). Higher and lower values can be suitable, depending on the bandwidth of irradiating radiation and the Raman shift values desired to be distinguished.

A tunable filter is useful when Raman scattering measurements are simultaneously made at multiple locations in the illuminated field and when a Raman spectrum (i.e., assessments at multiple RS values) is to be obtained using the detector (e.g., for collecting 2-dimensional RS data from a sample). A variety of filter mechanisms are available that are suitable for these purposes. For example, an Evans split-element liquid crystal tunable filter (LCTF) such as that described in U.S. Pat. No. 6,002,476 is suitable. An LCTF can be electronically controlled to pass a very narrow wavelength band of light. The spectral resolving power of 8 cm$^{-1}$ (0.25 nanometer) is suitable to perform Raman spectroscopy, and the image fidelity is sufficient to take full advantage of the resolving power of a light microscope, yielding a spatial resolution better than 250 nanometers. Other suitable filters include Fabry Perot angle-rotated or cavity-tuned liquid crystal (LC) dielectric filters, other LC tunable filters (LCTF) such as Lyot Filters and variants of Lyot filters including Solc filters, acousto-optic tunable filters, and polarization-independent imaging interferometers such as Michelson, Sagnac, Twynam-Green, and Mach-Zehnder interferometers. This list of suitable filters is not exhaustive.

Accommodation for Tissue Fluorescence

Tissues sometimes exhibit localized fluorescence which, if not accounted for, can complicate Raman spectral analysis. If such fluorescence occurs at a wavelength of interest for assessing the disease state of a cell in a sample, then a subtractive method can be used to correct for tissue fluorescence and prevent fluorescent emissions from obscuring relevant Raman scattering data.

In general, fluorescent emission is spectrally much broader than Raman scatter. For instance a typical Raman band in a cell sample will have a bandwidth of about 20 $cm^{-1}$. In contrast, the fluorescence spectrum (which can be tens to hundreds of nanometers in breadth) of the same cell sample irradiated with the same light will have a bandwidth of thousands of wavenumbers. Because of this, strategic choices of where in Raman shift space measurements are made (i.e., choice of which RS values are used for scattered light intensity measurements) permit correction for fluorescent emissions. By way of example, two image frames can be assessed in Raman space, one at 1584 $cm^{-1}$ (an RS value at which the cells scatter radiation) and another at 2600 $cm^{-1}$. If the cells exhibit substantially no Raman scattering at 2600 $cm^{-1}$, then the radiation detected in the frame assessed at 2600 $cm^{-1}$ will consist essentially only of radiation fluorescently emitted from the sample. The radiation detected in the frame assessed at 1584 $cm^{-1}$ will include both i) Raman scattered radiation and ii) fluorescently emitted radiation having substantially the same intensity as radiation fluorescently emitted at 2600 $cm^{-1}$. Subtracting the intensity of emissions assessed at 2600 $cm^{-1}$ from the intensity of emissions at 1584 $cm^{-1}$ will yield an intensity value essentially equal to the intensity of Raman scattered light at 1584 $cm^{-1}$. This is one example of a way by which the intensity of Raman scattered light from a sample can be assessed even if the sample also fluorescently emits light having the same wavelength as the Raman shifted light.

Materials present in cell and tissue samples obtained from humans or other mammals can interfere with Raman scattering of the cells of interest in the samples. These materials are preferably removed prior to Raman scattering analysis of the cells. By way of example, red blood cells (RBCs) exhibit strong Raman scattering at RS values including or overlapping 1581 $cm^{-1}$, and debris such as that which commonly occurs in bodily fluids or in excised samples can exhibit Raman scattering at a wide variety of RS values. RBC and debris can be removed from samples in relatively straightforward ways using known methods, such as gently rinsing cell samples with distilled, deionized water, normal saline, or dilute phosphate buffer. If RBCs are the cells being examined, then white blood cells (WBCs) and/or debris can be removed from the sample, using known methods (e.g., rinsing with distilled water or with an acetic acid solution), if Raman scattering by the WBCs and/or debris interferes with RBC Raman signals of interest.

Cells and Tissues

The methods described herein can be used to assess Raman scattering from substantially any cell for which a Raman scattering spectrum can be obtained. Use of the methods for assessment of the disease state of mammalian cells—especially human cells—is an important embodiment of the invention. However, the method can be used to assess Raman scattering from cells of plants, non-mammalian animals, fungi, protists, and monera. Samples containing cells of multiple types (e.g., a human tissue sample containing mycoplasma cells or a human kidney tissue sample including multiple cell types) can also be assayed, and Raman scattering data for the various cell types can be mapped together with microscopic image data, for example, to differentiate the cells.

The cells can be isolated cells, such as individual blood cells or cells of a solid tissue that have been separated from other cells of the tissue (e.g., by degradation of the intracellular matrix). The cells can also be cells present in a mass, such as a bacterial colony grown on a semi-solid medium or an intact or physically disrupted tissue. By way of example, blood drawn from a human can be smeared on the surface of a suitable Raman scattering substrate (e.g., an aluminum-coated glass slide) and individual cells in the sample can be separately imaged by light microscopy and Raman scattering analysis. Similarly a slice of a solid tissue (e.g., a piece of fresh tissue or a paraffin-embedded thin section of a tissue) can be imaged on a suitable surface.

The cells can be cells obtained from a subject (e.g., cells obtained from a human blood or urine sample, tissue biopsy, or surgical procedure). Cells can also be imaged where they naturally occur, such as by imaging the cells in an accessible location, imaging cells in a remote location using a suitable probe, or by revealing cells (e.g., surgically) that are not normally accessible.

Cells that are imaged can be alive or dead. Non-living extracellular matter, such as extracellular matrix and connective tissue fibers can also be imaged. Cells and other materials from which Raman spectral data are collected should not be treated in any way known to obscure a Raman spectral characteristic that is to be observed. By way of example, cells and other materials can be imaged in place, by assessing Raman-shifted light scattered from a tissue illuminated in situ in a living mammal. Such analysis can identify the disease state of a cell in the tissue. Analogous posthumous analysis of a cell or tissue can identify a disease state that led or contributed to mortality of the organism from which it was obtained.

Cells obtained from an organism can reflect exposure of the organism to a compound detectable by Raman spectroscopy (i.e., if the compound is associated with a tissue of the organism) or exposure to an environmental condition which influences the Raman spectrum of a cell or tissue type in the organism. By assessing these factors, the Raman imaging methods described herein can be used to differentiate individual organisms, to assess their exposure to Raman-active compounds, or to assess their exposure to certain environmental conditions.

Raman Scattering by Bladder Cancer Cells

In one embodiment, the invention includes the discovery that normal and cancerous bladder cells can be differentiated from one another by their Raman spectral features.

Normal, non-cancerous ladder cancer cells exhibit significant Raman scattering at an RS value of about 1584 $cm^{-1}$, relative to non-cancerous bladder cells. The intensity of Raman scattering at this RS values increases with increasing grade of bladder cancer. Other RS values at which Raman scattering is associated with the cancerous state of bladder cells include about 1000, 1100, 1250, 1370, and 2900 $cm^{-1}$. This list of values is not exhaustive. Furthermore, there is a generalized increase in Raman scattering at RS values in the range from about 1000 to 1605 $cm^{-1}$ and in the range from about 2750 to 3200 $cm^{-1}$ in bladder cancer cells, relative to non-cancerous bladder cells, and this generalized increase is more pronounced in the range of RS values from about 1530 to 1605 $cm^{-1}$. These RS values and ranges are useful for assessing the cancerous state of bladder cells.

Raman Scattering by Sickled Red Blood Cells

In another embodiment, the invention includes the discovery that normal and sickled red blood cells (RBCs) can be differentiated from one another by various Raman spectral features.

RBCs exhibit a dynamic Raman spectral response to illumination. The initial Raman spectrum of an RBC (i.e., the spectra observable in about the first 100 milliseconds after the onset of illumination) changes as illumination continues until a stable (i.e., substantially unchanging) Raman spectrum occurs within a few seconds after the onset of illumination (e.g., after one to two seconds or less, depending on the intensity of the illuminating radiation). Normal and sickled RBCs exhibit Raman spectral differences in both their initial and stable Raman spectra. Changes in both initial and stable spectra of normal and sickled RBCs, as well as differences in the dynamic changes in the Raman spectra of both cell types upon illumination can be used to differentiate normal and sickled RBCs.

The Raman spectral features of sickled RBCs can be detected regardless of whether the RBC has assumed the characteristic crescent shape that RBCs of patients afflicted with sickle cell anemia assume under certain physiological conditions (e.g., low oxygen tension). The Raman spectral features of sickled RBCs can be used to identify RBCs from a patient who is homozygous for the sickle cell trait gene or a patient who is heterozygous for that gene. In heterozygotes, both normal and sickled hemoglobin are produced. For RBCs obtained from a heterozygote, an averaged Raman spectrum intermediate between the Raman spectra disclosed herein for normal and sickled RBCs can be expected, the intensities of the characteristic features depending on the proportions of normal and sickled hemoglobin produced by the patient.

FIGS. 8-11 show the initial and stable spectra of RBCs obtained from an individual whose genome does not include an allele of the sickle cell trait gene and from another individual who is homozygous for the sickle cell trait gene. The spectra are averaged spectra obtained from 16 fields of view, each of which fields included 3-5 RBCs. Spectra corresponding to sickled RBCs are averaged spectra from fields which included at least one RBC that had the characteristic crescent shape.

In the initial spectra (i.e., spectra obtained not more than 100 milliseconds following the onset of illumination), sickled RBCs exhibit at least three Raman spectral peaks that are shifted relative to the corresponding peaks in normal RBCs. The first is a peak that occurs at about 1086 cm$^{-1}$ in normal RBCs, but at about 1070 cm$^{-1}$ in sickled RBCs. The second is a peak that occurs at about 996 cm$^{-1}$ in normal RBCs, but at about 991 cm$^{-1}$ in sickled RBCs, and a difference in the peak width can also be seen, with the 991/996 cm$^{-1}$ peak being broader for normal RBCs. The third is a peak that occurs at about 671 cm$^{-1}$ in normal RBCs, but at about 666 cm$^{-1}$ in sickled RBCs. Other differences in the initial spectra of normal and sickled RBCs can be seen in the spectra shown in FIG. 8.

Figure 9:
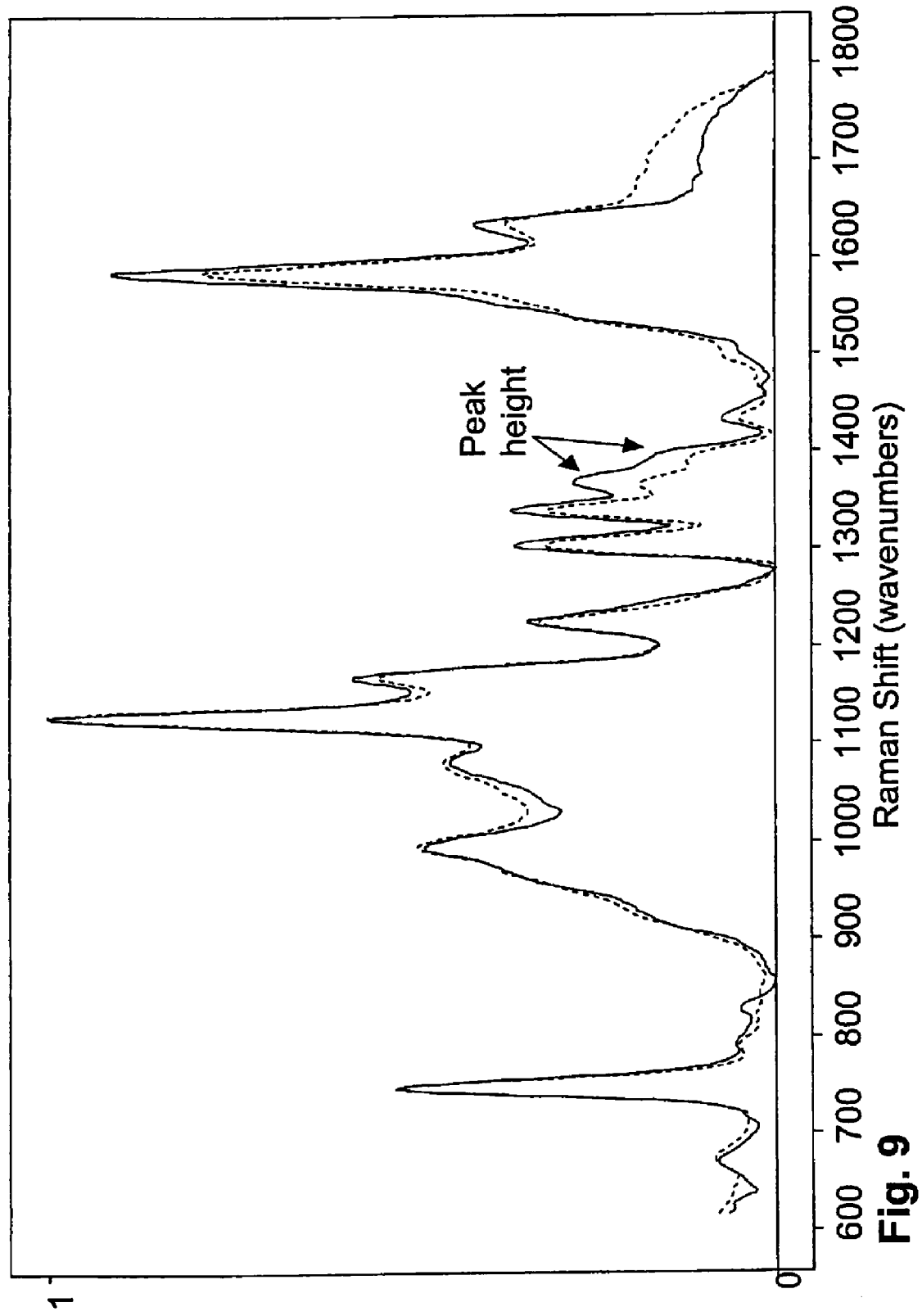
FIG. 9 is a graph of averaged Raman scattering intensity over a range of Raman shift values for normal RBCs (solid line) and for RBCs (including at least one sickled RBC) obtained from a patient with sickle cell disease (dashed line). The Raman spectra for these cells were obtained after a illuminating the cells for a sufficient period (about 2-5 seconds) that the Raman spectral response of the cells remained stable over time. Spectra obtained from 16 fields of view, each including 3-5 RBCs, were averaged to produce these data.

In the stable spectra (i.e., spectra after at least 2-5 seconds following the onset of illumination), the intensities of at least two Raman spectral peaks exhibited by sickled RBCs differ from the intensities of the corresponding peaks exhibited by normal RBCs. The first is a peak that occurs at about 1366 cm$^{-1}$, and the second is a peak that occurs at about 1389 cm$^{-1}$, as can be seen in FIG. 9. Other differences in the stable spectra of normal and sickled RBCs can be seen in the spectra shown in FIG. 9.

Figure 10:
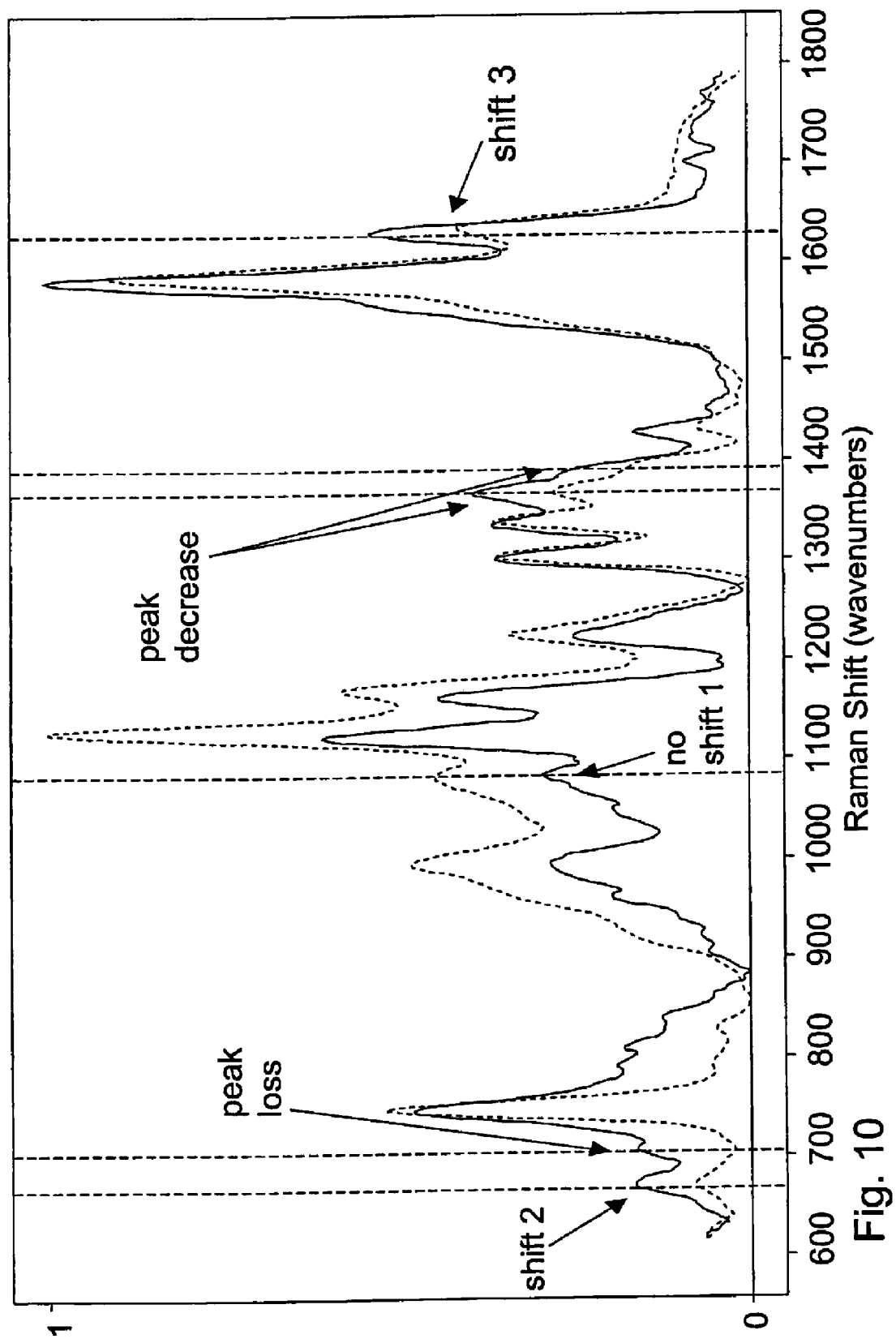
FIG. 10 is a graph of averaged Raman scattering intensity over a range of Raman shift values for normal RBCs that had been illuminated for analysis of Raman scattering for not more than 100 milliseconds (solid line). The Raman scattering intensity is also shown (dashed line) for the same RBCs that had been illuminated for a sufficient period (about 2-5 seconds) that their Raman spectral response remained stable over time. Spectra obtained from 16 fields of view, each including 3-5 RBCs, were averaged to produce these data.
Figure 11:
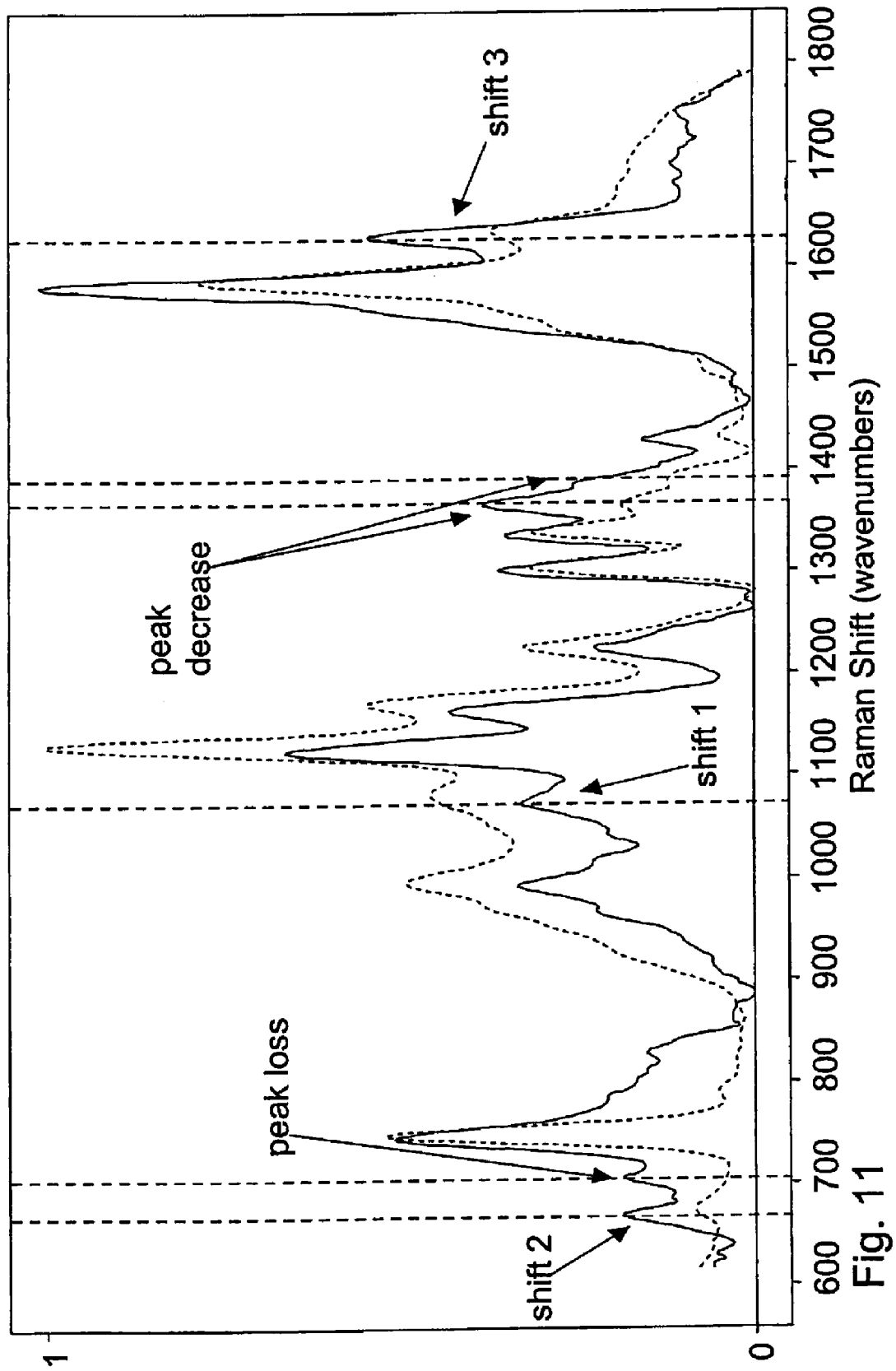
FIG. 11 is a graph of averaged Raman scattering intensity over a range of Raman shift values for RBCs (including at least one sickled RBC) obtained from a patient with sickle cell disease. The RBCs had been illuminated for analysis of Raman scattering for not more than 100 milliseconds (solid line). The Raman scattering intensity is also shown (dashed line) for the same samples that had been illuminated for a sufficient period (about 2-5 seconds) that their Raman spectral response remained stable over time. Spectra obtained from 16 fields of view, each including 3-5 RBCs, were averaged to produce these data.

Normal and sickled RBCs can also be distinguished by the dynamic response of Raman-shifted light scattered by the respective cells. As indicated in FIG. 10, normal RBCs do not exhibit a significant dynamic shift in the RS value of the peak at about 1082 cm$^{-1}$ or the peak at about 676 cm$^{-1}$. Comparing FIGS. 10 and 11, it can be seen that both normal and sickled RBCs exhibit a dynamic loss of the peak at about 706 cm$^{-1}$, and a shift in the RS value of a peak that initially occurs at about 1629 cm$^{-1}$ to about 1636 cm$^{-1}$. Similarly, dynamic decreases in peak heights are observed at RS values of about 1366 cm$^{-1}$, 1385 cm$^{-1}$, and 1437 cm$^{-1}$ for both normal and sickled RBCs, but the dynamic changes are greater at the peaks at RS values of about 1366 cm$^{-1}$, 1385 cm$^{-1}$ in sickled RBCs than in normal RBCs.

The differences disclosed herein regarding the Raman spectral characteristics of normal and sickled RBCs can be used to differentiate the two cell types, or to confirm such differentiation by other methods (e.g., by microscopic observation of RBC morphology). The devices and methods used herein can be coupled with a device to sort, ablate, or otherwise treat normal and sickled RBCs, to achieve differential treatment of such cells.

Raman Scattering by Cardiac Tissue

In another embodiment, the invention includes the discovery that Raman spectral characteristics of regions of cardiac tissue can be used to differentiate cardiac tissue having different disease states. For example, cardiac tissues of patients afflicted with idiopathic heart failure can be distinguished from patients afflicted with ischemic heart failure.

At least two types of tissue structures can be distinguished in cardiac tissues. First, bundles of muscle cells form a contractile fibrous matrix which provides the pumping impetus to the cardiac tissue. Second, connective tissues in the heart provide structure and support for the contractile cardiac muscle tissue, connect cardiac muscle fibers to one another, and form valves and other internal barriers within the heart.

FIGS. 12-15 show Raman spectral characteristics of cardiac muscle and connective tissues of patients afflicted with idiopathic or ischemic heart failure. As expected, based on the differential composition of cardiac muscle and connective tissues, the two tissue types exhibit different Raman spectra. However, these figures also demonstrate that the Raman spectra of the two tissue types can be used to distinguish cardiac tissues of patients afflicted with idiopathic heart failure (presumably including at least some patients with genetically-encoded defects in cardiac tissue components) from cardiac tissues of patients afflicted with ischemic heart failure.

The Raman spectral characteristics of cardiac tissues described herein can be used to diagnose a condition in a patient, to confirm a diagnosis made by other means, to predict susceptibility to cardiac disease, or to assess the cause of death of an individual post mortem. Because the methods described herein are able to identify the type cardiac tissue (e.g., connective tissue or cardiac muscle tissue) associated with heart failure, they can be used to assess the likely efficacy of various forms of therapy. By way of example, some forms of idiopathic heart failure are believed to arise from loss of structural integrity of connective tissues, such as in patients whose genomes include certain genetically-encoded forms of collagen that are less stable or strong than others. Identification of loss of connective tissue integrity in a patient's heart suggests that therapeutic options contributing to the physical geometric support of the heart may be preferable to options which improve cardiac muscle contractility, at least in that patient.

The Raman spectral features of cardiac tissues disclosed herein for patients afflicted with ischemic heart failure are not believed to be exhibited exclusively by patients with ischemic heart failure. Ischemic heart failure is attributable to physiological defects other than cardiac muscle and cardiac connective tissue defects. For example, many instances of ischemic heart failure are attributable to vascular pathologies. For that reason, the Raman spectral data described herein for cardiac tissue samples obtained from patients afflicted with ischemic heart failure can be expected to be exhibited by ischemic cardiac tissue, regardless of the cause of the ischemia. Because cardiac ischemia attributable to vascular disease can be a local phenomenon (i.e., only affecting certain areas of the heart), the samples obtained from patients afflicted with ischemic faiure may represent relatively normal cardiac tissues, albeit under the conditions of global ischemia caused by a poorly functioning heart. At least some Raman spectral features of such tissue can be exhibited by patients who are afflicted with other forms of cardiac ischemia, such as myocardial infarction and angina pectoris.

Figure 12:
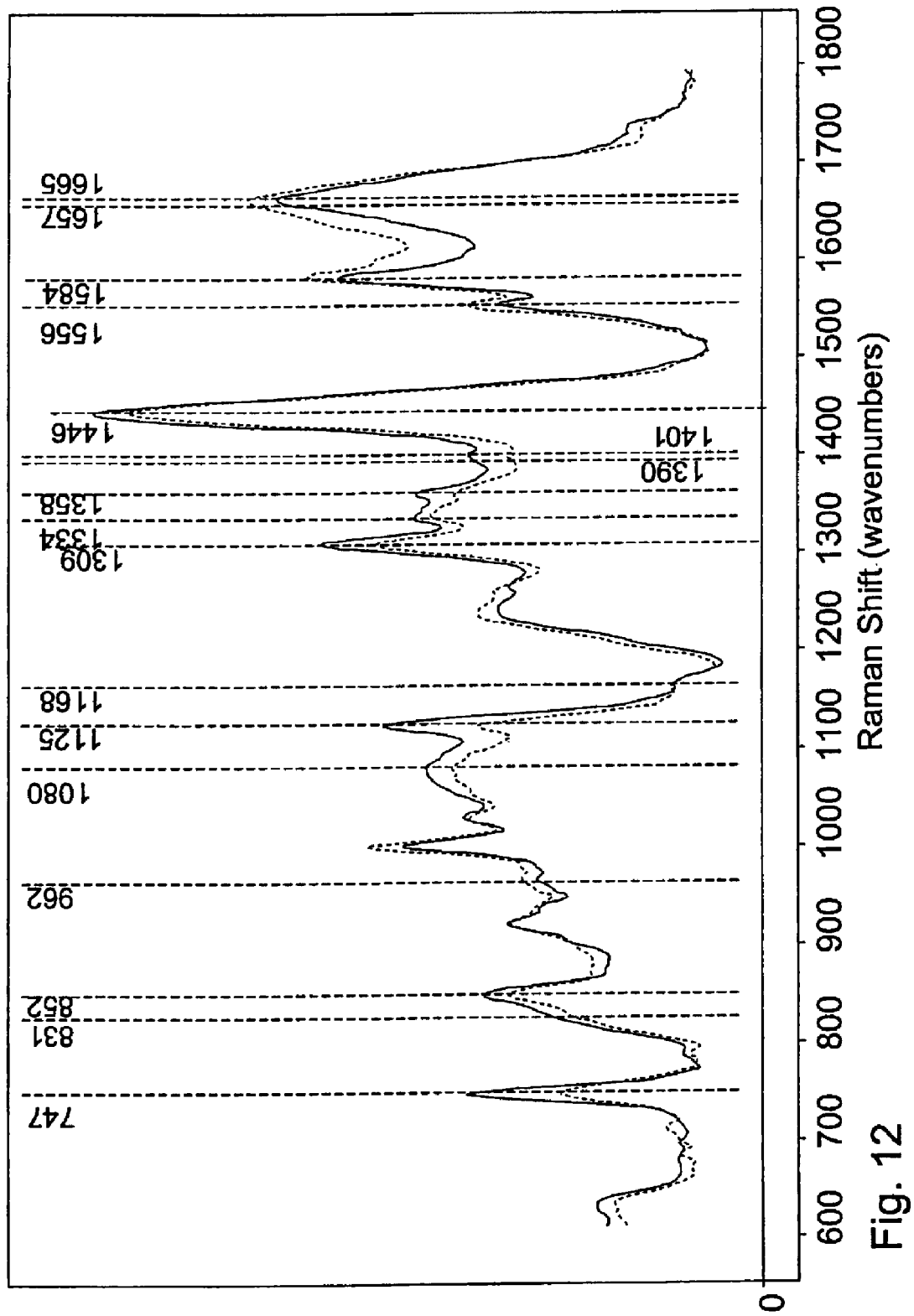
FIG. 12 is a graph of averaged Raman scattering intensity over a range of Raman shift values for connective tissue fibers in cardiac tissue samples obtained from patients afflicted with either idiopathic heart failure (solid line) or ischemic heart failure (dashed line). The graphs represents averaged Raman scattering intensity data obtained from five patients afflicted with idiopathic heart failure and averaged Raman scattering intensity data obtained from five patients afflicted with ischemic heart failure.

As can be seen from examining FIG. 12, the Raman spectrum of cardiac connective tissue from patients afflicted with idiopathic heart failure can be differentiated from the Raman spectrum of the same tissue from patients afflicted with ischemic heart failure. For example, Raman spectral peaks at 747 $cm^{-1}$, 1080 $cm^{-1}$, 1125 $cm^{-1}$, 1309 $cm^{-1}$, and 1358 $cm^{-1}$ differ. The width of Raman peaks at 1584 $cm^{-1}$ and 1665 $cm^{-1}$ can also be used as a basis for differentiating the tissues. Because cardiac ischemia, is not expected to significantly alter the structure of cardiac connective tissue in patients in which it occurs (other than at foci of ischemic insult, at which scar tissues can form), the Raman spectrum of the connective tissue from patients afflicted with ischemic heart failure can be expected to be substantially the same as that of tissue in patients with non-diseased cardiac tissue. Thus, the Raman spectral characteristics disclosed herein for cardiac connective tissue from patients afflicted with idiopathic heart failure can be used to diagnose, predict, or confirm (e.g., by autopsy) occurrence in a patient of a connective tissue defect associated with heart failure.

Figure 13:
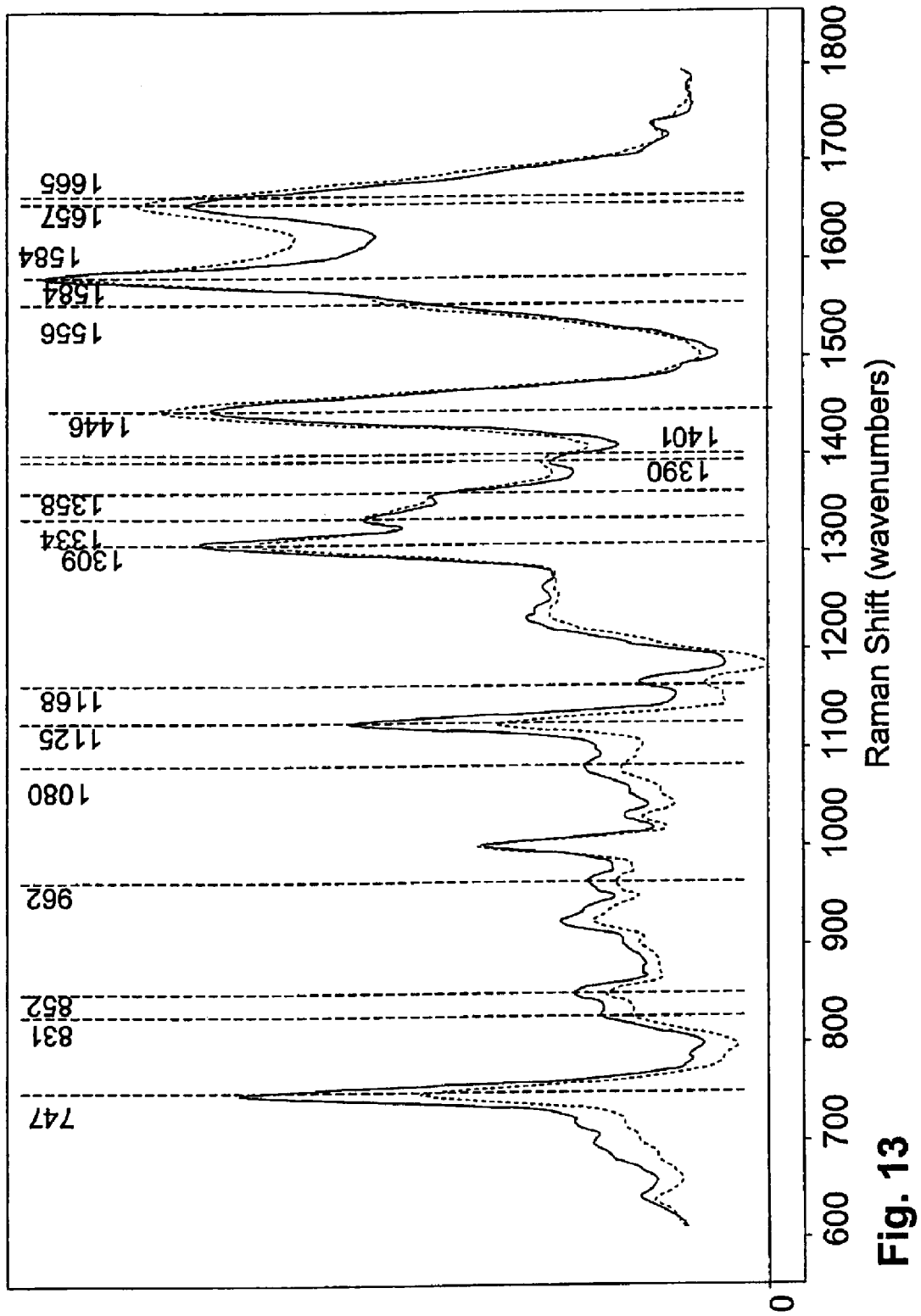
FIG. 13 is a graph of averaged Raman scattering intensity over a range of Raman shift values for cardiac muscle cell bundles in cardiac tissue samples obtained from patients afflicted with either idiopathic heart failure (solid line) or ischemic heart failure (dashed line). The graphs represents averaged Raman scattering intensity data obtained from five patients afflicted with idiopathic heart failure and averaged Raman scattering intensity data obtained from five patients afflicted with ischemic heart failure.

The data shown in FIG. 13 indicate that fewer Raman spectral differences are evident between cardiac muscle tissue from patients afflicted with idiopathic heart failure and cardiac muscle tissue from patients afflicted with ischemic heart failure. This is as expected, because cardiac muscle tissue from most patients afflicted with heart failure (of whatever etiology) can be expected to show evidence of ischemia. Nonetheless, the differences between the Raman spectral characteristics of cardiac muscle tissues from patients of the two types indicate differences in cardiac muscle tissue that can account for at least some of the heart failure that is otherwise considered "idiopathic." Comparing the spectra in FIG. 13, differences can be seen in the widths of Raman spectral peaks at RS values of about 1584 $cm^{-1}$ and 1665 $cm^{-1}$. In addition, the RS value of the peak at 1080 $cm^{-1}$ (in cardiac muscle tissue obtained from patients afflicted with ischemic heart failure) is narrower in spectral data corresponding to patients afflicted with idiopathic heart failure and is proportionally less intense (relative to the ischemic heart failure samples) at slightly lower RS values, such as 1078 $cm^{-1}$. The Raman spectral characteristics disclosed herein for cardiac muscle tissue can be used to diagnose, predict, or confirm (e.g., by autopsy) occurrence in a patient of a cardiac muscle tissue defect associated with heart failure.

Figure 14:
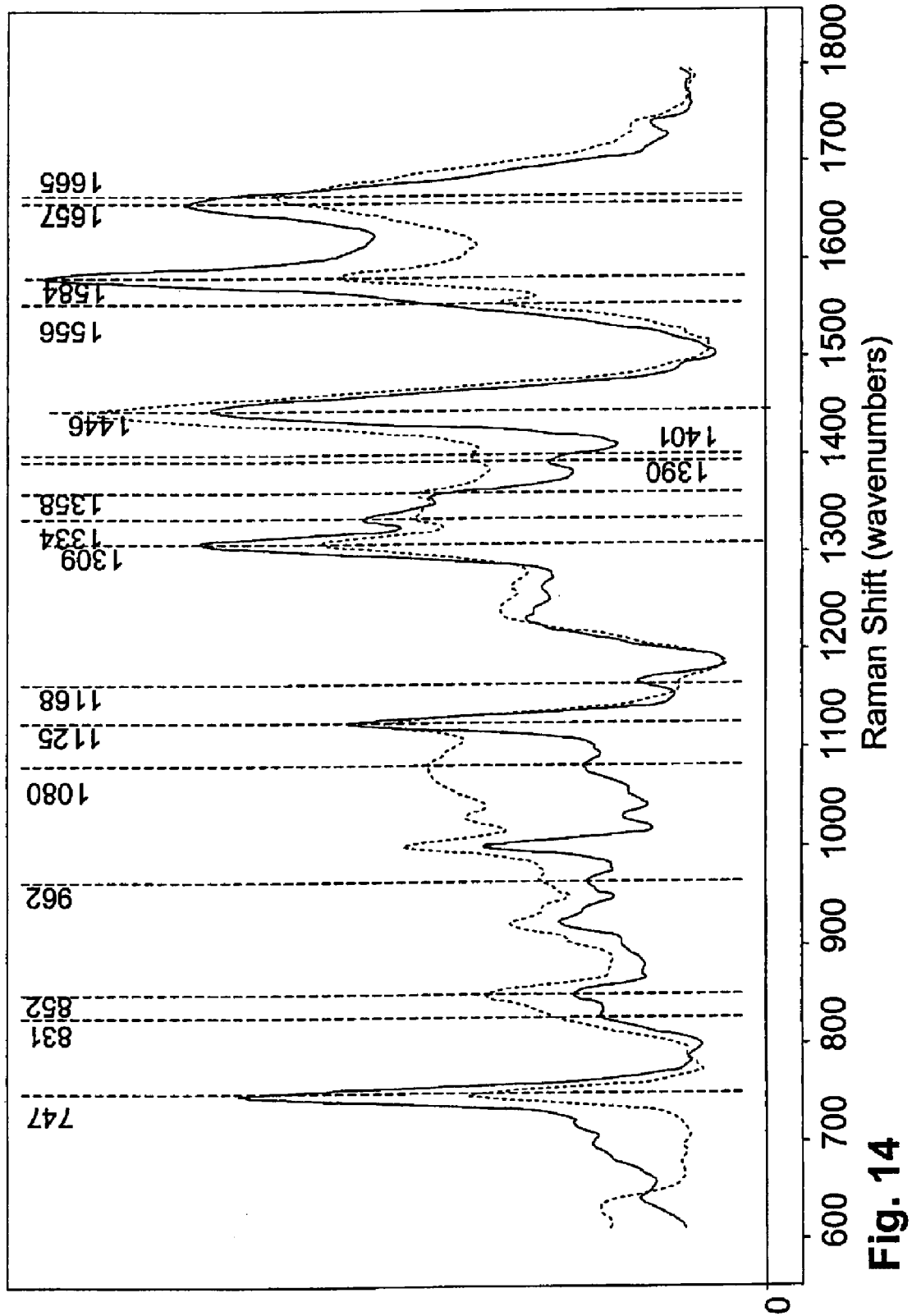
FIG. 14 is a comparison of averaged Raman scattering intensity between cardiac muscle cell bundles (solid line) and connective tissue fibers (dashed line) in cardiac tissue samples obtained from patients afflicted with idiopathic heart failure.
Figure 15:
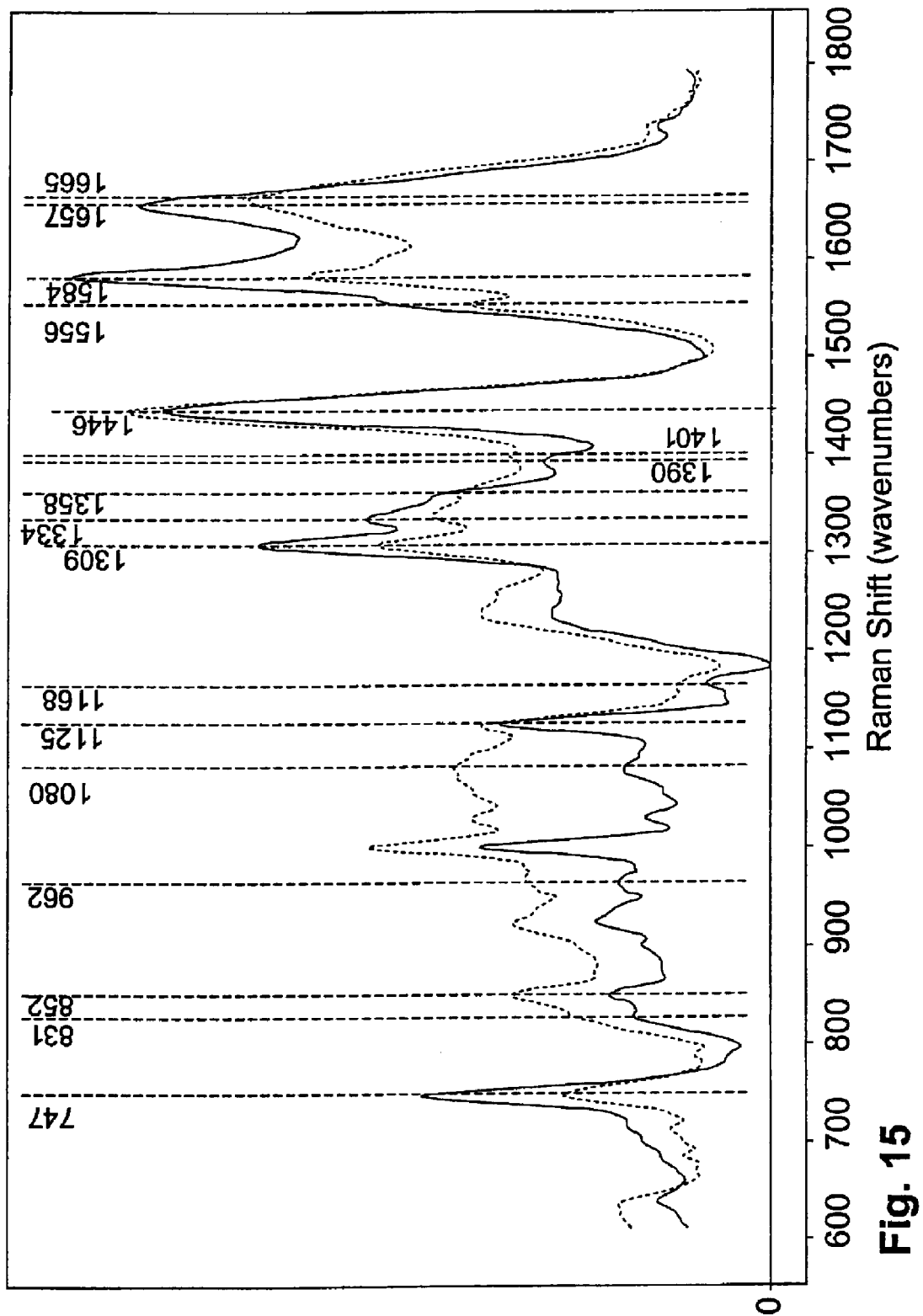
FIG. 15 is a comparison of averaged Raman scattering intensity between cardiac muscle cell bundles (solid line) and connective tissue fibers (dashed line) in cardiac tissue samples obtained from patients afflicted with ischemic heart failure.

As shown in FIGS. 14 and 15, there are significant Raman spectral differences between spectra obtained from cardiac muscle tissue and cardiac connective tissue, whether the cardiac tissue was obtained from patients with ischemic or idiopathic heart failure. Examples of these differences include: better resolution of peaks at 831 $cm^{-1}$ and 852 $cm^{-1}$ in the muscle tissue; occurrence of a peak at 1168 $cm^{-1}$ in muscle tissue; better distinction in the muscle tissue between the 1390 $cm^{-1}$ and 1401 $cm^{-1}$ peaks; sharper definition of the 1556 $cm^{-1}$ in connective tissue; and occurrence in connective tissue of a broad underlying band between about 800 $cm^{-1}$ and 1200 $cm^{-1}$. These spectral differences demonstrate that the methods described herein can be used to differentiate tissue sub-types within a broader tissue type (e.g., cardiac connective tissue can be differentiated in a microscopic image of a cardiac tissue sample from cardiac muscle tissue in the same sample.

Raman Scattering by Kidney Tissue

In another embodiment, the invention includes the discovery that Raman spectral characteristics of regions of prostate tissue can be used to differentiate normal, malignant, and benign kidney tissues, as well as kidney tissue afflicted with end stage renal disease.

Figure 17:
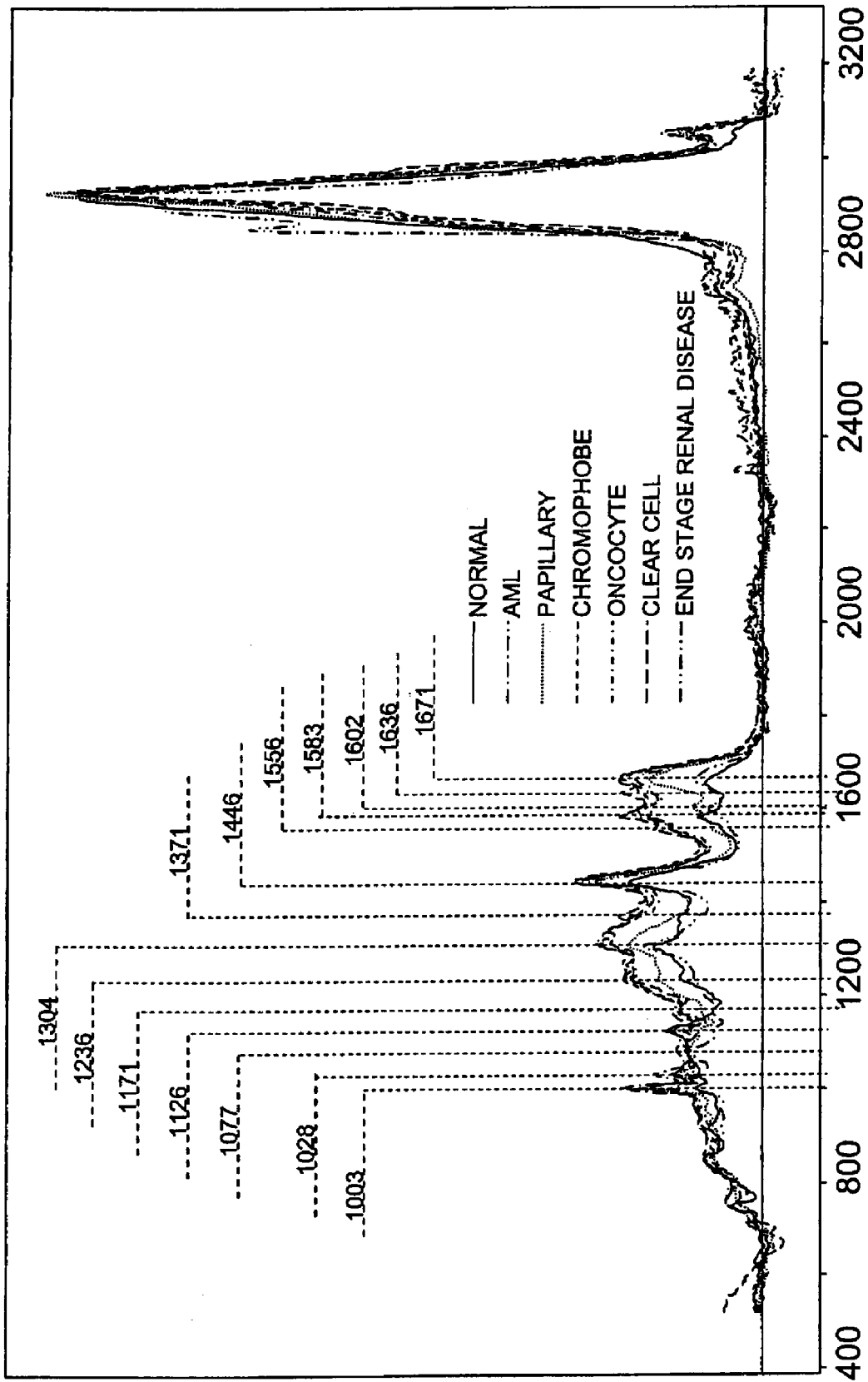
FIG. 17 is a comparison of Raman scattering intensity among various types of normal and cancerous kidney cells. The line styles corresponding to the kidney cell spectra obtained are shown in the figure.

FIG. 17 shows differences in Raman spectra obtained from various kidney tissue samples. These spectral differences evident in this figure demonstrate that the methods described herein can be used to differentiate normal and diseased kidney tissues.

Raman Scattering by Prostate Tissue

In another embodiment, the invention includes the discovery that Raman spectral characteristics of regions of prostate tissue can be used to differentiate cancerous and benign prostate tissues.

Figure 16A:
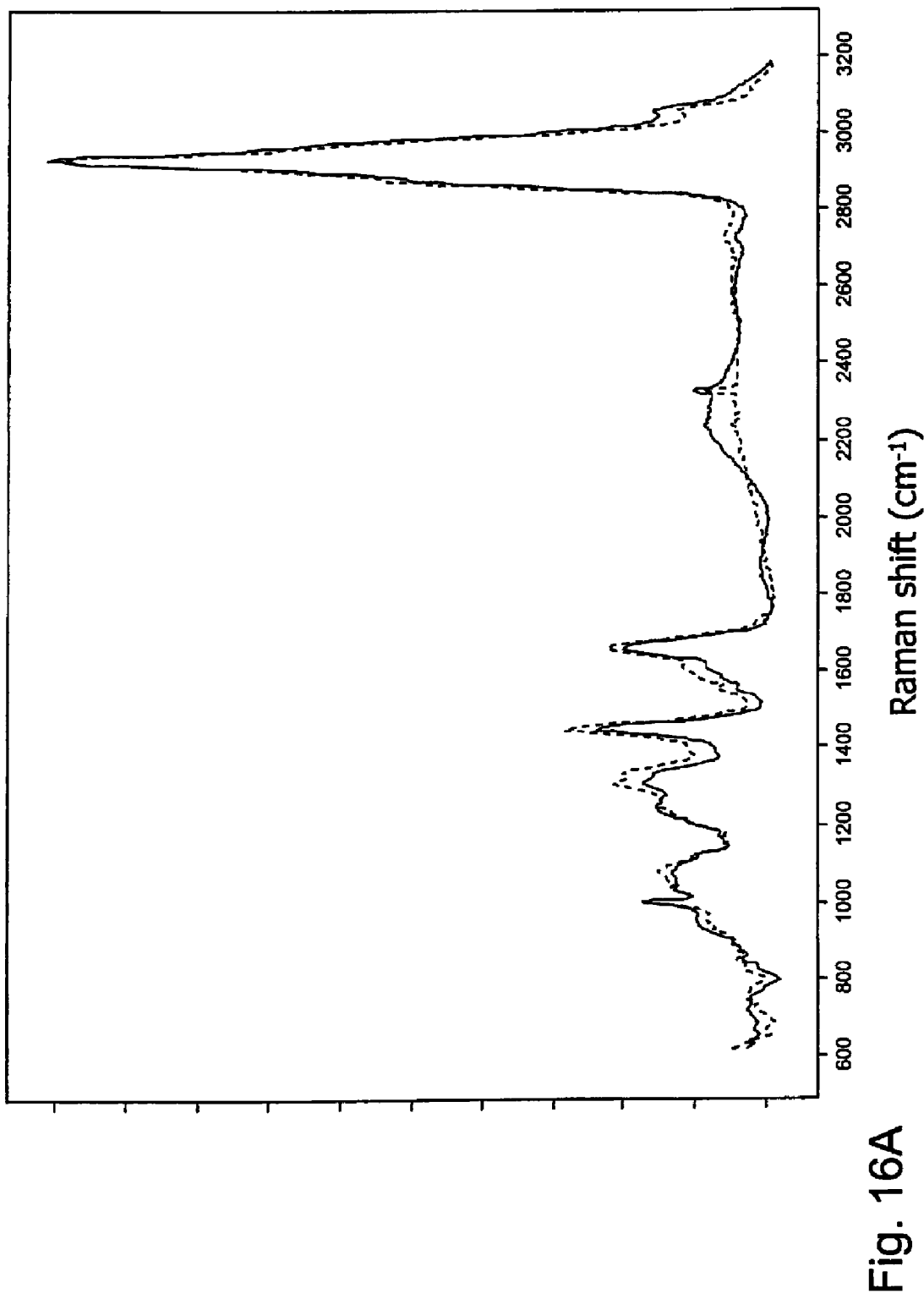

FIG. 16 shows differences in normalized Raman spectra obtained from cancerous and benign prostate tissue samples. For example, cancerous prostate tissue samples exhibit lower Raman scattering intensities at RS values of about 1080, 1300, and 1600 $cm^{-1}$. Other spectral differences are evident from the figure. These spectral differences demonstrate that the methods described herein can be used to differentiate cancerous and benign prostate tissues.

Raman Scattering by Diseased Cell Types

It was discovered that diseased cells exhibit enhanced Raman scattering at the RS values disclosed herein, relative to the corresponding non-diseased cells. Examples of diseased cells which can be differentiated from non-diseased cells of the same type using the methods described herein include cancerous kidney cells (e.g., cancerous renal tubular cells), cancerous prostate cells, cancerous colon cells, cancerous breast cells, cancerous lung cells, cancerous bone marrow cells, cancerous brain cells, cells of inflamed tissues, cells of tissues undergoing autoimmune attack, and cardiac muscle cells of diseased heart tissue (e.g., ischemic heart tissue). The methods described herein can be used to assess the diseased state of cells of at least these types by assessing Raman scattering by the cells at RS values in the range 280 to 1800 $cm^{-1}$ and/or 2750-3200 $cm^{-1}$ or at the particular RS values indicated herein. For instance, the range of RS values from 500 to 1800 $cm^{-1}$ is informative for several disease types disclosed herein. Comparison of Raman scattering at those RS values with reference values or with non-diseased cells of the same type can indicate the diseased state of the sampled tissue.

Without being bound by any particular theory of operation, it is believed that tissues for which a diseased state can be detected using the methods described herein exhibit altered metabolic activity, relative to corresponding non-diseased cells of the same type. The altered metabolic activity is thought to be attributable to one or more disease processes occurring in the tissue. For instance, in an inflamed tissue or organ, an altered metabolic activity is required to mount the inflammatory response to the inciting event. This response drives the cells/tissues into a state of altered metabolic activity, further altering the biochemical makeup of the cell. These alterations are manifested in the Raman scattering characteristics of the cells or tissues. An implication of this theory of operation is that the methods disclosed herein should be useful for differentiating diseased and non-diseased tissue for many (and potentially all) diseases that are characterized by altered basal metabolism.

The methods described herein can also be used to determine the type and/or origin of cells found within the body by assessing Raman scattering characteristics of the cells and comparing them with the known Raman scattering characteristics of various cell types. In this way, the origin of a cancerous metastasis can be determined or migration of non-cancerous cells from a body location at which they normally occur to an abnormal body location can be detected.

The cells analyzed as described herein can be substantially any cells that can be obtained from, or accessed, in a mammal such as a human. Such cells can be cells obtained from a body fluid (e.g., urine, saliva, sputum, feces, blood, mucus, pus, semen, and fluid expressed from a wound or vaginal fluid), cells obtained by rinsing a body surface (e.g., a bronchial or peritoneal lavage), cells of a fresh tissue sample (e.g., scraped, biopsied, or surgically removed tissue), cells of paraffin-embedded or otherwise archived tissue samples, or cells that are examined in vivo in the mammal. The cells can be individual cells, clumps of cells, or cells that exist in a matrix of other cells and/or extracellular matrix.

Cells to be analyzed as described herein should be placed on and secured to a surface to prevent movement during analysis, unless the cells tend to adhere to the surface on their own. This is particularly important if Raman spectroscopy and light microscopy data are to be combined, because it is important to be able to correlate the microscopic characteristics of the cells, as directly or indirectly (e.g., using computer-processed or -stored image data) observed with the Raman scattering exhibited by the same cells. Cells can be secured or fixed on a surface using substantially any known technique, and any reagents known to exhibit strong Raman scattering at the RS values disclosed herein should be avoided or accounted for in scattering intensity determinations. Cells can be secured or fixed as individual cells on a substrate, as a substantially flat layer or slice of cells on a substrate, or as a three-dimensional mass of cells. When a secured or fixed cell preparation includes cells at different elevations above the surface of the substrate, spatial analysis of the preparation is possible using known adaptations to light microscopy and Raman scattering methods. By way of example, Raman scattering can be correlated with height above the substrate by assessing Raman scattering using different planes of focus. Information obtained at the various planes can be reconstructed (e.g., using a computer for storage and display of the information) to provide a two- or three-dimensional representation of the sample.

Raman scattering analysis can be assessed for cells in vivo, for example using an insertable and removable fiber-optic probe (e.g., a fiberscope such as that described in U.S. Pat. No. 6,788,860). The probe can be fixed in place relative to the cells being assessed using known methods, and such fixation should employed if reproducible accessing of the cells is desired. For example, if cells are to be assessed in vivo to determine their disease status and cells determined to be diseased are thereafter to be ablated by delivery thereto of intense laser illumination, then it is important that the probe not be displaced relative to the cells during the interval between determination of disease status and ablation.

Combined Raman Spectroscopic Analysis and Visible Light Microscopy

Cellular imaging based on optical spectroscopy, in particular Raman spectroscopy, can provide a clinician with important information. Such techniques can be performed ex vivo (e.g., on raw, fixed, or mounted body fluids, cells, tissues, or biopsies) or in vivo (e.g., using endoscopic techniques). Molecular imaging simultaneously provides chemical morphological information (i.e., size, shape and distribution) for molecular species present in the sample. Using Raman spectroscopic imaging, a trained clinician can determine the disease state of a tissue or cellular sample based on recognizable changes in chemical morphology without the need for sample staining or modification.

By contrast, visible light microscopy offers the trained clinician only physical morphological and structural clues regarding the disease state of the cells or tissue being examined. Use of colored or fluorescent dyes can provide limited information regarding the cell surface or internal constituents of the cells, and can aid in determining the identity (i.e., cell or tissue type) or biochemical makeup of the cells. However, many staining reagents and methods can alter the morphology and/or structure of cells and tissue, thereby destroying useful information even as they reveal other information. Furthermore, many staining reagents and methods cannot practically be used for in vivo imaging or imaging of cells.

Combining Raman spectroscopy and visual light microscopy techniques enhances the usefulness of each by adding context to the information generated by the separate methods. Thus, physical morphological and structural information derivable from microscopic examination can be understood in the context of the biochemical makeup of the corresponding cellular materials and Raman scattering-based clues to the disease state and/or metabolic state of the cells being examined. If desired, staining or labeling reagents can be used in combination with Raman scattering and light microscopy in order to yield further information about the cells.

By way of example, the presence of micrometastases in lymph nodes draining bladder tissue provide important information regarding the stage and metastatic potential of a bladder tumor, which information can be used to select an appropriately aggressive anti-cancer treatment. However, differentiating between bladder cells and other cells which may occur in a lymph node can be difficult, as can differentiating between cancerous and non-cancerous bladder cells. Using the methods described herein, bladder cells in a lymph node can be identified using microscopic techniques (e.g., using a bladder cell-specific staining reagent such as a labeled monoclonal antibody) and Raman scattering spectroscopy can be used to assess the cancerous state of any bladder cells identified in the lymph node. Alternatively, Raman scattering techniques can be used both to identify cell type (i.e., by assessing characteristic Raman spectral properties of cells) and to determine the disease status of the cells that are present.

Substantially any Raman spectrometer capable of defining, detecting, or capturing data from cell- and tissue-scale samples can be used to generate the Raman scattering data described herein. Likewise, substantially any light microscopy instrument can be used to generate visible light microscopy information. In circumstances in which positions of cells in the sample can be correlated (e.g., by analysis of cell position and/or morphology or by analysis of indicia on or shape of the substrate), it is not necessary that the Raman and microscope be integrated. In such circumstances, the data collected from each instrument can be aligned from separate observations. Preferably, however, a single instrument includes the Raman spectroscopy and light microscopy functionalities, is able to perform both analyses on a sample within a very short time period (e.g., less than one hour, preferably less than 10 minutes or 1 minute), and is able to correlate the spatial positions assessed using the two techniques. Information gathered using such an instrument can be stored in electronic memory circuits, processed by a computer, and/or displayed together to provide a depiction of the cell sample that is more informative than the separate depictions of the information obtained by the two techniques. A suitable example of equipment having these characteristics is the FALCON (RTM) RMI microscope available from ChemImage Corp. (Pittsburgh, Pa.). Suitable instruments are also described in U.S. Pat. No. 6,002,476 and in co-pending U.S. patent application Ser. No. 09/619,371.

A visible light microscope is not the only instrument which can be used in conjunction with a Raman spectrometer to analyze cells as described herein. Substantially any spectroscopic instrument can be used cooperatively with a Raman spectrometer, so long as at least some portion of the field of view of each instrument can be correlated with a portion of the field of view of the other. By way of example, a Raman spectrometer can be coupled with both a visible light microscope and a fluorescent spectrometer, using the same optics (e.g., as in the FALCON (TM) microscope system of ChemImage Corp.) or different optical paths. Data collected using the Raman and fluorescent spectrometers can be combined with visual data collected using the visible light microscope, for example by i) correlating the intensity of red shading of one or more portions of the visible microscopic field with the intensity of Raman scattered light at a selected RS value originating from the portion(s) and ii) correlating the intensity of green shading of one or more portions of the visible microscopic field with the intensity of fluorescent light at a particular wavelength emitted from the portion(s). By combining the information obtainable from multiple spectroscopic instruments, multiple optical properties of cells can be determined. A non-limiting list of such optical properties include absorbance, fluorescence, Raman scattering, and polarization characteristics. These devices and techniques can also be used to determine morphological and kinetic properties of cells, such as their shape and movement. Each of the properties thus determined can be used to assess the disease state of the cell, for example by comparison with properties of cells known to be diseased or non-diseased.

An example of a probe suitable for in vivo analysis of cells in a mammal is described in co-pending U.S. patent application Ser. No. 10/184,580 (publication no. US 2003/0004419, which is incorporated herein by reference). The tip of the probe can be inserted near or against a tissue of interest and Raman scattering and visible microscopic image data can be collected therefrom, optionally at various discrete depths using focusing techniques and/or at various RS values. Substantially any fiber optic or other optical probe that can deliver irradiation to a tissue in vivo and collect Raman light scattered therefrom can be adapted to an appropriate Raman spectrometer to perform the methods described herein. The probe preferably also includes an optical channel (e.g., a common optical fiber or a separate one) to facilitate microscopic imaging of the same tissue for which Raman spectroscopy is performed.

Information generated from Raman spectroscopy and/or light microscopy as described herein can be stored in electronic memory circuits, such as those of a computer, for storage and processing. A wide variety of data analysis software packages are commercially available. Suitable types of software include chemometric analysis tools such as correlation analysis, principle component analysis, factor rotation such as multivariate curve resolution, and image analysis software. Such software can be used to process the Raman scattering and/or visible image data to extract pertinent information that might otherwise be missed by univariate assessment methods.

Images of spectral information obtained from a single field of view of a sample can be combined in a straightforward manner if the images are obtained using the same optical path. For instance, a multimodal imaging instrument such as the FALCON (TM) Raman imaging microscope of ChemImage Corp. (Pittsburgh, Pa.) can be used to obtain Raman, fluorescent, and visible light reflectance image data from a sample using the same field of view and substantially the same optical path). Spatial alignment of spectral images can be as simple as overlying the spectral images from a single field of view, optionally with minor automated or manual alignment of image features.

EXAMPLES

The invention is now described with reference to the following Examples. These Examples are provided for the purpose of illustration only, and the invention is not limited to these Examples, but rather encompasses all variations which are evident as a result of the teaching provided herein.

Example 1

Raman Scattering Analysis of Bladder Cancer Cells.

Raman molecular imaging (RMI) was used to distinguish cancerous and non-cancerous bladder cancer cells to demonstrate that RMI is useful for detection of bladder cancer.

RMI is an innovative technology that combines the molecular chemical analysis capacity of Raman spectroscopy with the power of high definition digital image microscopic visualization. This platform enables physicians and their assistants to identify both the physical architecture and molecular environment of cells in a urine sample and can complement or be used in place of current histopathological methods.

The data presented in this example demonstrate that the Raman scattering signal from bladder cancer tissue and cells voided in the urine can be identified and be distinguished from normal bladder tissue and cells. Detectable differences between high and low grade tumor cells were observed. These data establish that RMI signatures of bladder cancer cells are viable for discriminating high and low grades of bladder cancer, so that the disease can be detected in its earliest stages. These results demonstrate that RMI can be used as a non-invasive screening tool for detection of bladder cancer, for example in high risk populations (e.g., smokers over 40 years of age).

The experimental data presented below were derived from measurements made using a FALCON (TM) RMI microscope obtained from ChemImage Corp. (Pittsburgh, Pa.). The FALCON (TM) system uses 532 nanometer laser light to illuminate a sample over a wide field and collects Raman image data at multiple Raman shift (RS) values using a liquid crystal tunable filter (LCTF) unit equipped with a cooled charge-coupled device (CCD) array detector. This system is capable of collecting Raman spectra of the entire field of view and simultaneously acquiring Raman imaging spectral data and dispersive spectral data, as described in U.S. Pat. No. 6,717,768. Those features permit selection between full-field imaging and full-field collection of spectral data using a single set of optics. Data was processed using the CHEMIMAGE ANALYZE (TM) 6.0 spectral image processing software obtained from ChemImage Corp., applying standard techniques for signal processing and multivariate spectral data reduction techniques.

Samples were derived from anatomical pathology specimens retained in a cryogenic tissue bank. Sections of tissue samples embedded in TISSUE-TEK OCT (RTM) (10.24% w/w polyvinyl alcohol; 4.26% w/w polyethylene glycol; 85.50% w/w non-reactive ingredients; obtained from Saura Finetek USA., Torrence, Calif.) were cut using a cryomicrotome at a thickness of 10 micrometers and placed on optical quality fused silica microscope slides. Excess OCT was removed with deionized water, and slides were air dried.

Figure 2:
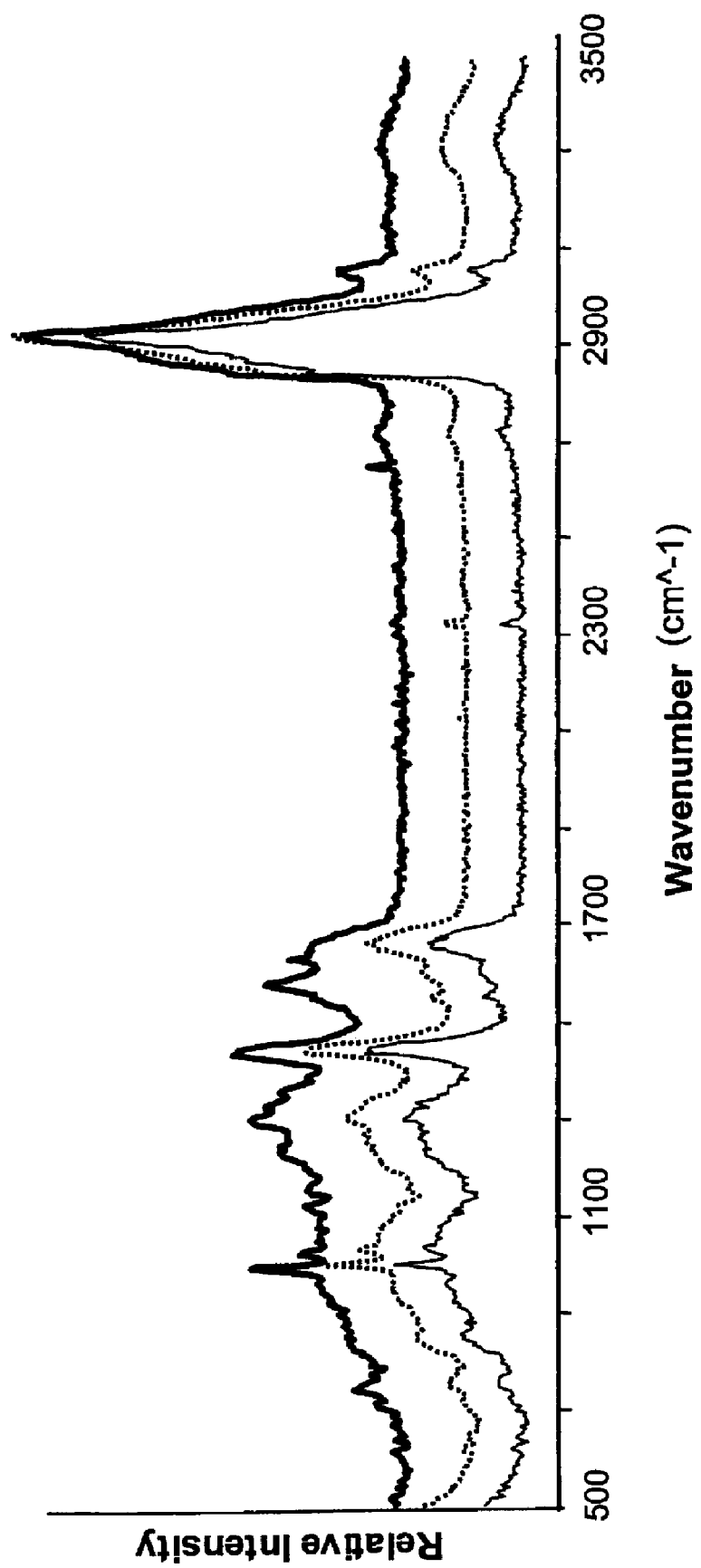
FIG. 2 is a graph of Raman scattering intensity over a range of Raman shift values for bladder cells obtained from a healthy patient (thin solid and dotted lines) and for bladder cells obtained from a patient afflicted with bladder carcinoma (thick solid line). The baselines of the spectra are offset to facilitate comparison.

FIG. 2 shows the Raman spectra of bladder mucosal cells obtained from two patients not afflicted with bladder cancer (thin solid and dotted lines in FIG. 2) and from one patient afflicted with bladder carcinoma (thick solid line in FIG. 2).

The Raman spectra shown in FIG. 2 indicate the reproducibility of spectra for normal (non-cancerous) mucosa. Significant differences between the Raman spectra of the normal samples and the mucosal sample obtained from the patient afflicted with bladder carcinoma can be seen, for example at Raman shift values in the range from about 1000 to 1605 $cm^{-1}$, and more pronounced in the region from about 1525 to 1605 $cm^{-1}$. These data indicate that bladder carcinoma cells can be differentiated from normal bladder mucosal cells by RMI.

Figure 3:
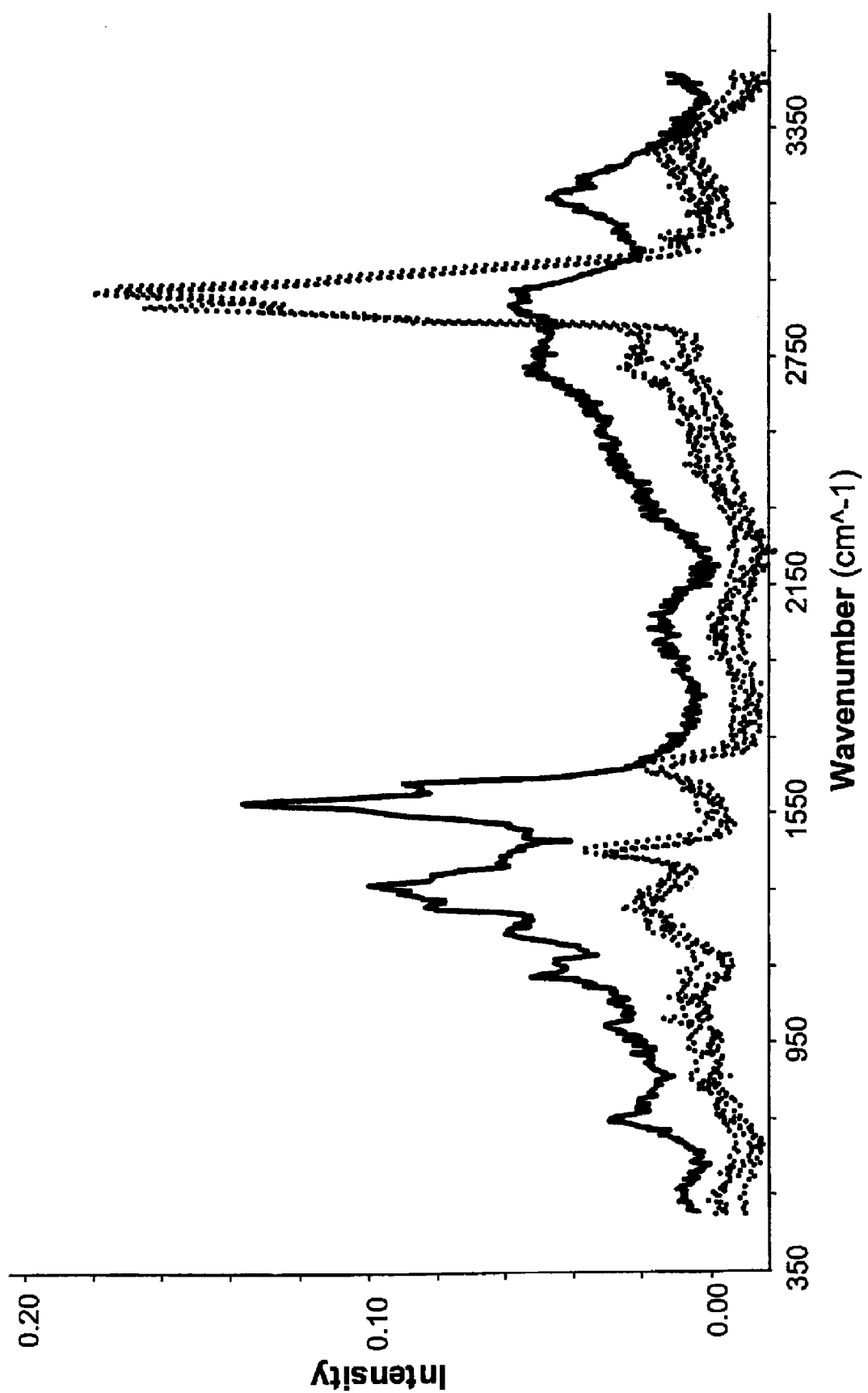
FIG. 3 is a graph of Raman scattering intensity over a range of Raman shift values for normal (i.e., non-cancerous) bladder tissue (dotted lines) and grade 3 transitional cell carcinoma bladder tissue (solid line).

FIG. 3 shows the differences between the Raman spectra for three normal bladder mucosa tissue samples and a grade 3 transitional cell carcinoma (TCC) tissue. Significant Raman scattering intensity differences (between normal and TCC bladder mucosa tissues) were observed at Raman shifts of about 1000, 1250, 1370, and 1584 $cm^{-1}$.

Smears of cells from the grade 3 TCC bladder mucosa were prepared by manually pressing the tissue against the slide and dragging it across the aluminum surface. Raman spectra of the smears were obtained, and the spectra were found to be reproducible among the smears prepared. Furthermore, the Raman spectra obtained using smears were virtually identical to the Raman spectra obtained using intact tissue samples. These results indicate that the RMI method is not highly sensitive to the method used to prepare the cells for imaging, meaning that relatively simple cytological preparative methods can be employed.

Once the ability to recognize reproducible results from tissues had been established, single cell monitoring methods, investigating cells shed in urine, were used. Red blood cells (RBCs) and other suspended or soluble substances present in normal urine can interfere with RMI. For example, RBCs exhibit Raman scattering peaks at Raman shifts (wavenumber values) of 1380 $cm^{-1}$ and 1590 $cm^{-1}$. It was found to be desirable to rinse cells (e.g., with distilled water) prior to RMI in order to avoid interference from RBCs, cell and tissue debris, and other potentially interfering substances in urine. This was performed by collecting cells from urine samples by centrifugation, rinsing the collected cells with distilled, deionized water, again centrifuging, and re-suspending the cells. A drop of the cell suspension was placed on an aluminum-coated microscope slide and smeared using another slide. In tissue sections, paraffin should also be removed as thoroughly as possible.

Microscopic inspection of cells obtained from urine samples indicated that there were white blood cells (WBCs) present. Raman spectra of WBCs and transitional epithelium are distinguishable from the Raman spectra of normal bladder mucosal cells. Nonetheless, it is preferable to remove WBCs from urine samples prior to assessing Raman scattering data from the remaining cells. Even if WBCs are not removed from the sample, their morphology and Raman scattering characteristics can be used to distinguish them from other cells in the sample.

Figure 4A:
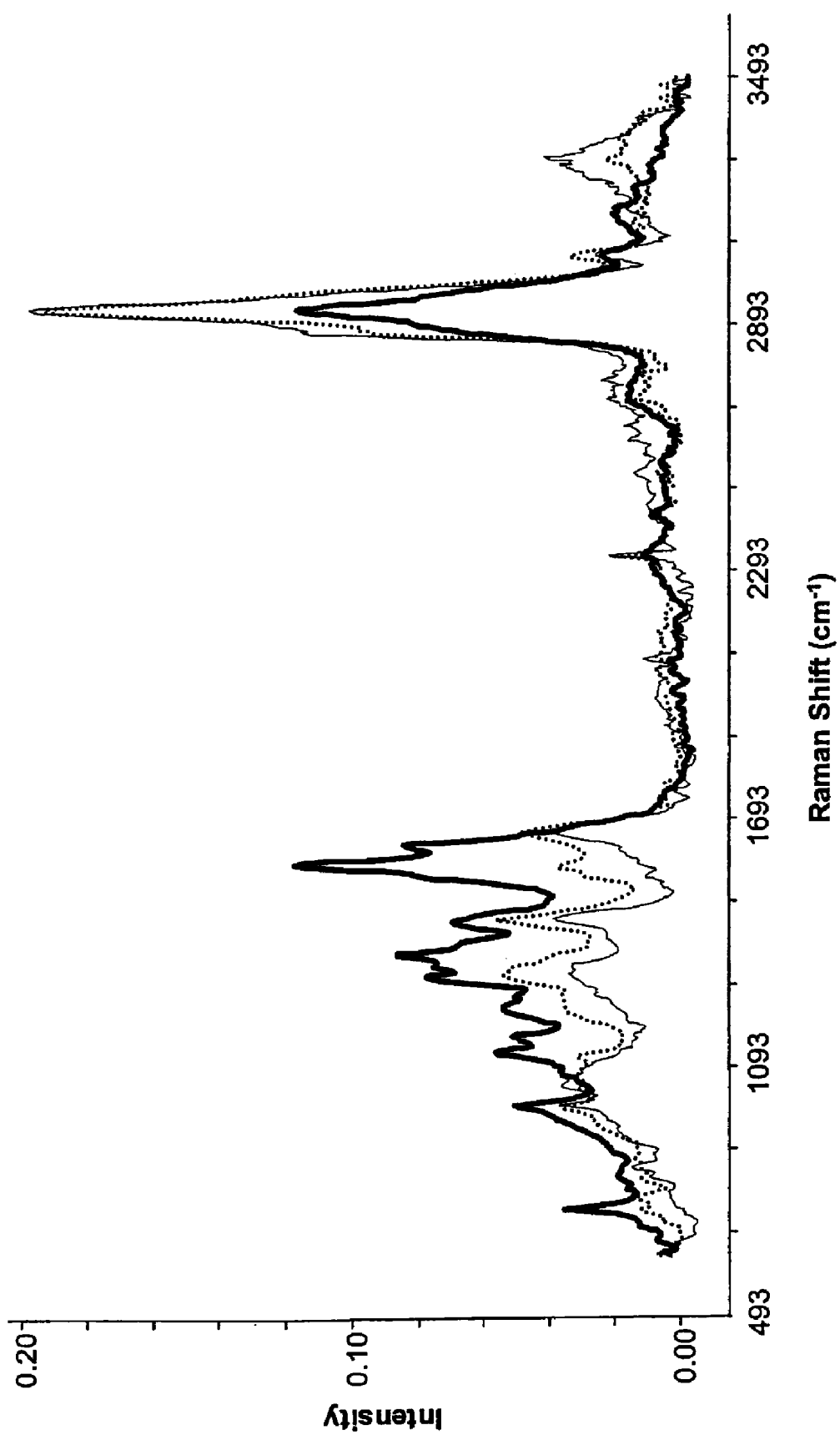
FIG. 4A is a graph of Raman scattering intensity over a range of Raman shift values for bladder cells collected from urine of a healthy patient (thin solid line), bladder cells collected from urine of a patient afflicted with low grade (grade 1) bladder cancer (dotted line), and bladder cells collected from urine of a patient afflicted with high grade (grade 3) bladder cancer (thick solid line). The baselines of the spectra are offset to facilitate comparison. The baselines of the spectra are offset to facilitate comparison.
Figure 4B:
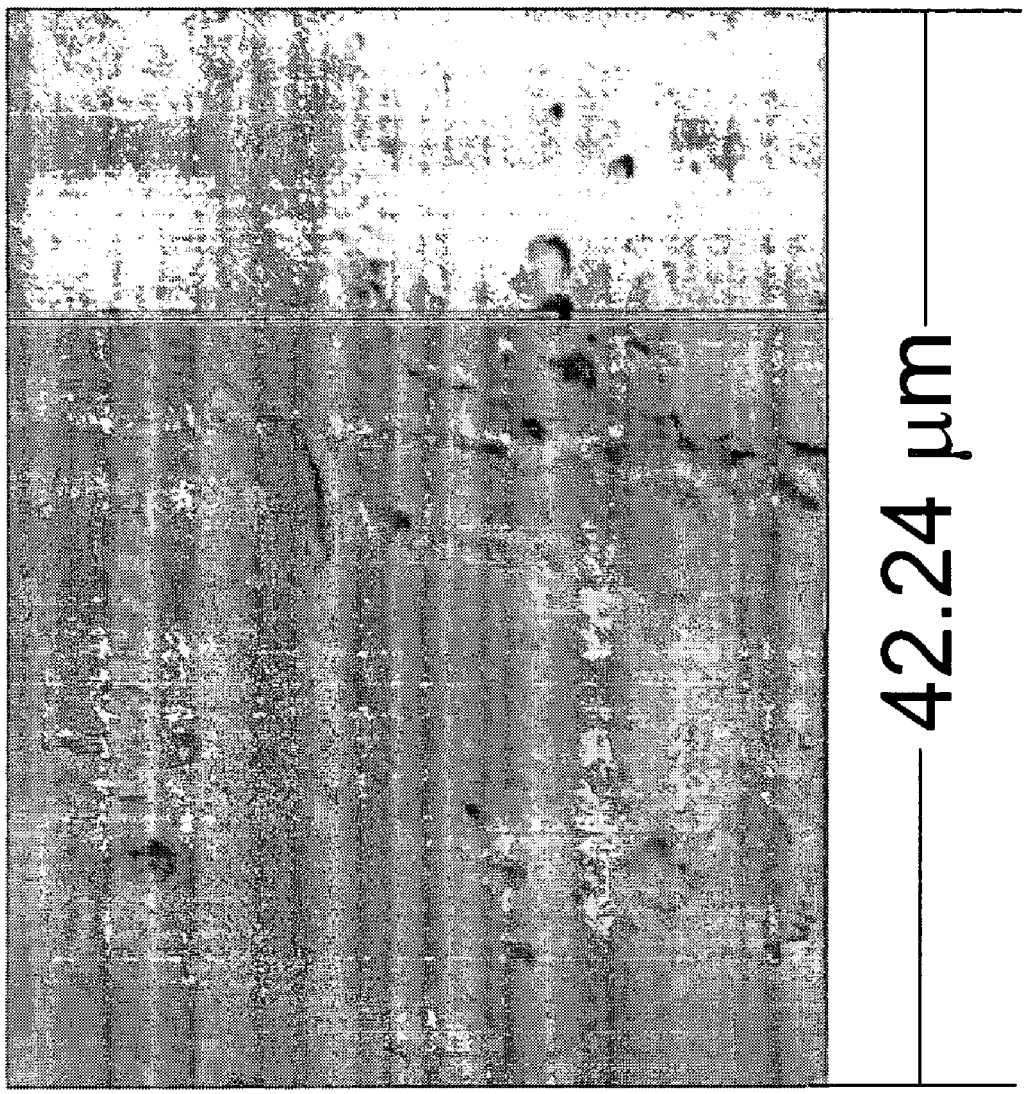
FIGS. 4B, 4C, and 4D are micrographs of a bladder cell collected from urine of a healthy patient (4B), a bladder cell collected from urine of a patient afflicted with low grade (grade 1) bladder cancer (4C), and a bladder cell collected from urine of a patient afflicted with high grade (grade 3) bladder cancer (4D).
Figure 4C:
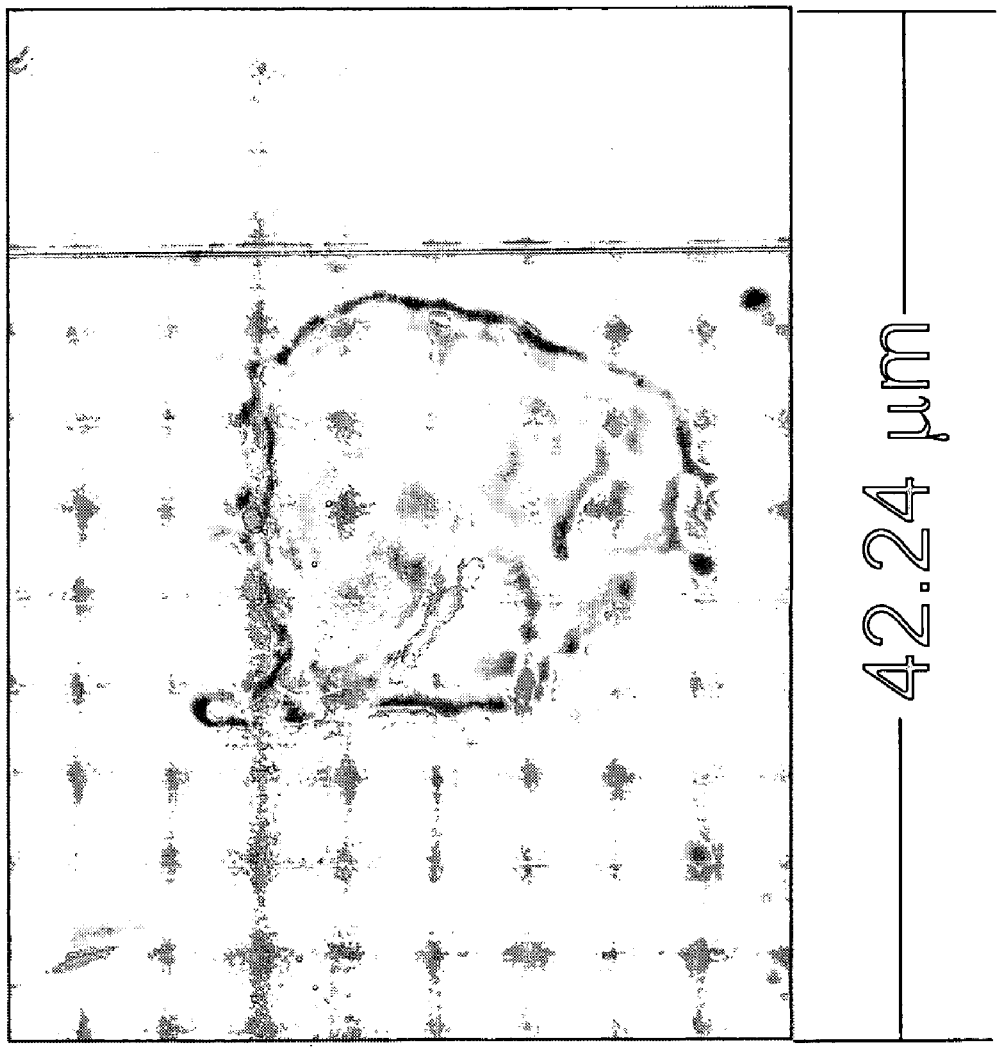
Figure 4D:
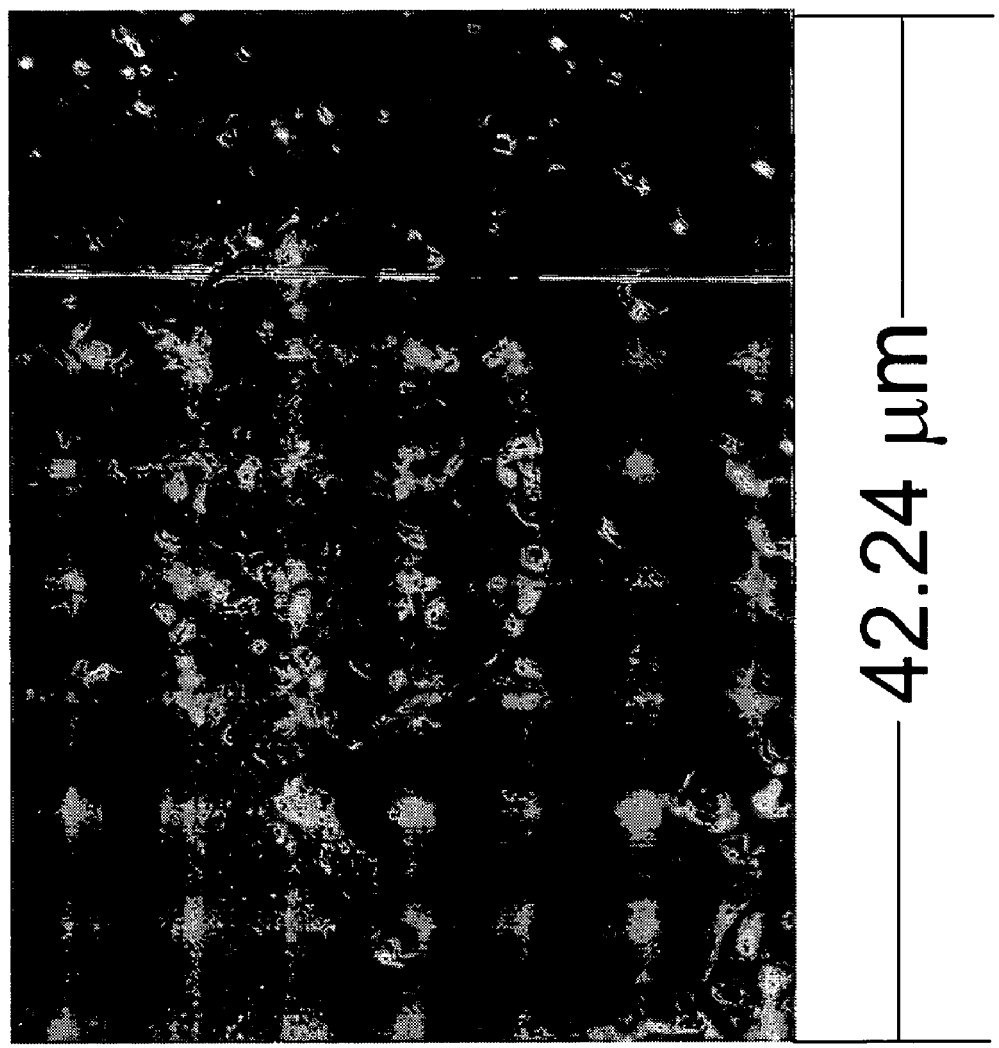
Figure 5:
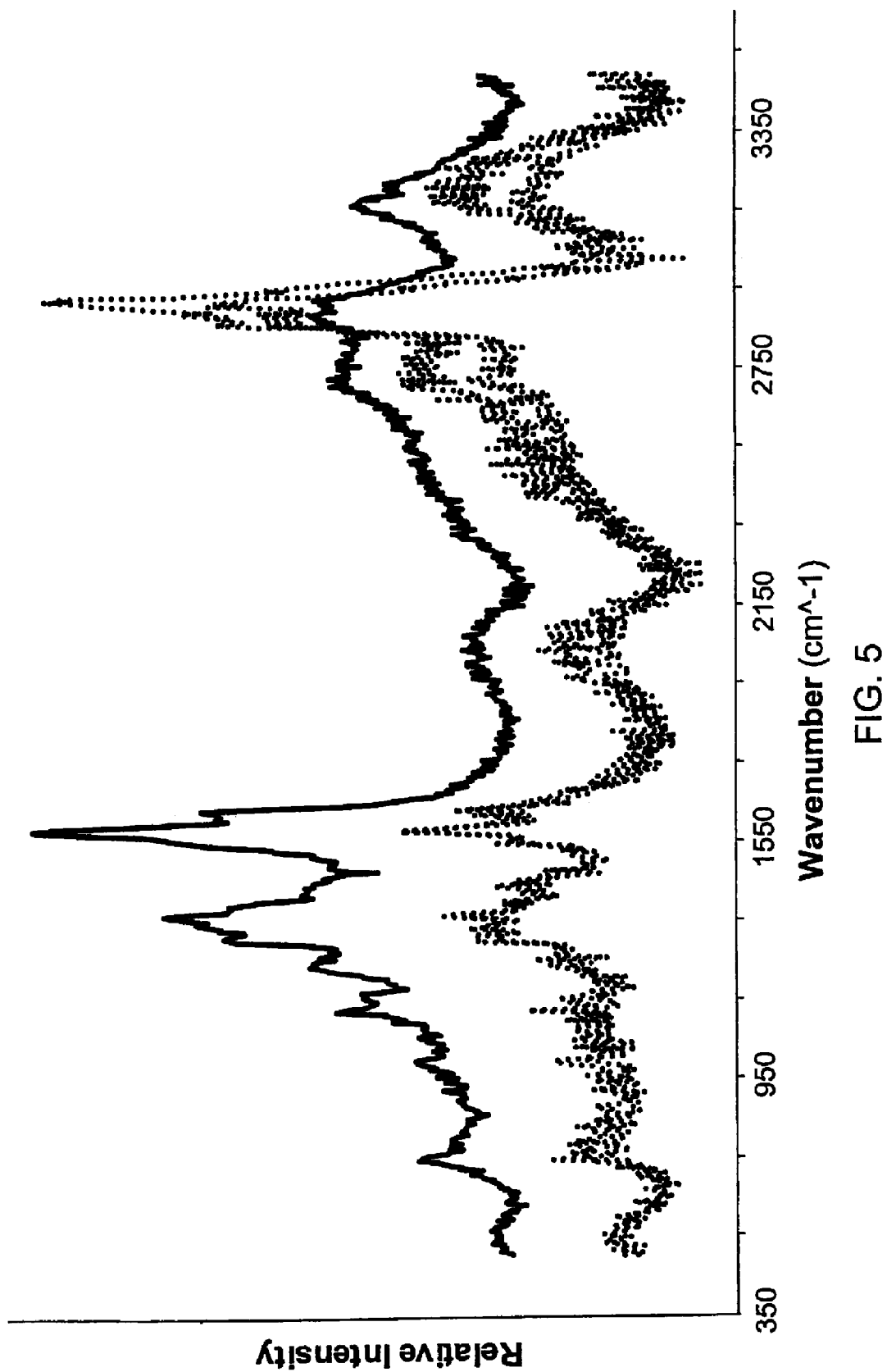
FIG. 5 is a graph of Raman scattering intensity over a range of Raman shift values for bladder cells collected from urine of two patients afflicted with grade 2 bladder cancer (dotted lines), and bladder cells collected from urine of a patient afflicted with grade 3 bladder cancer (solid line). The baselines of the spectra are offset to facilitate comparison.
Figure 6:
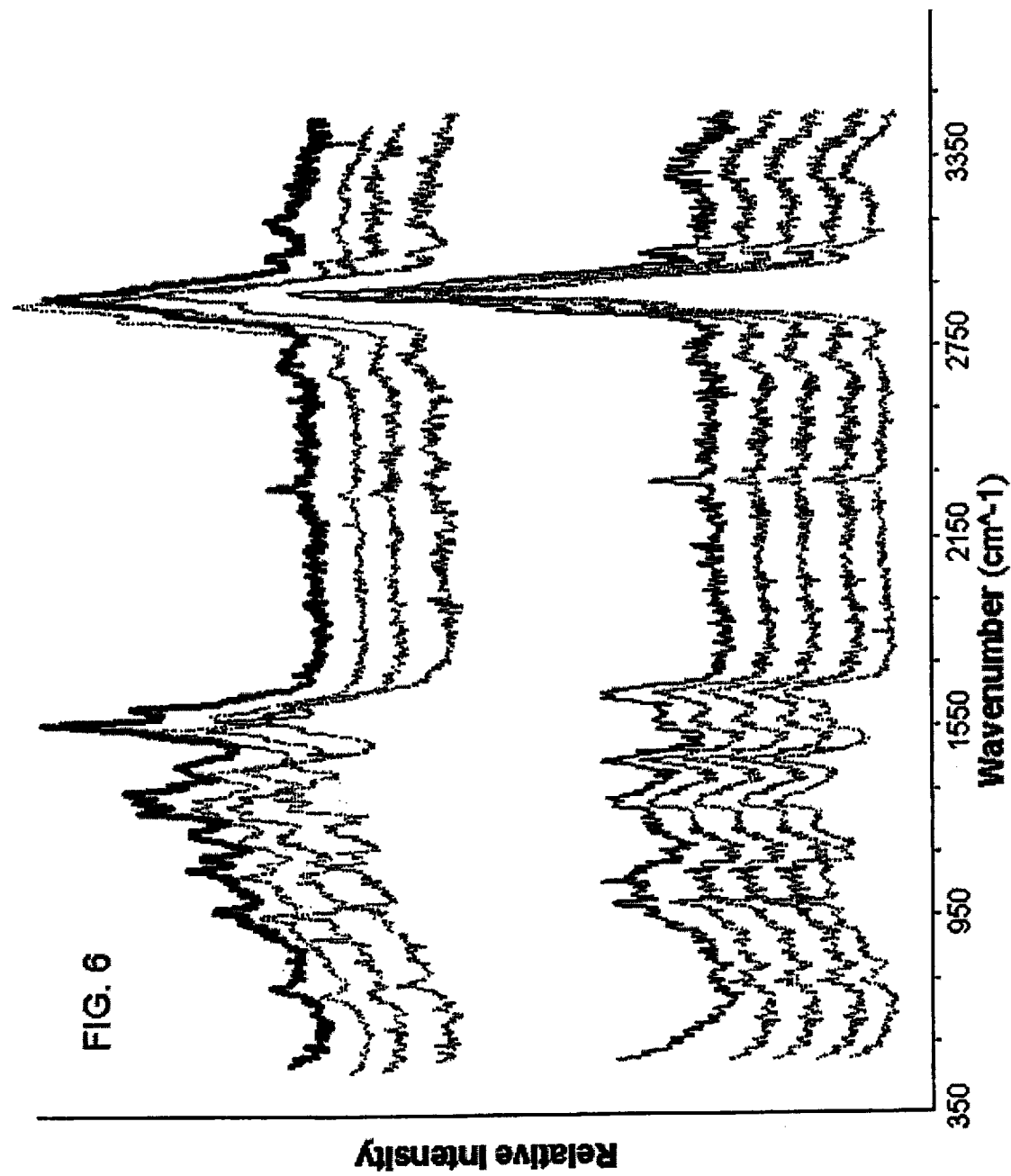
FIG. 6 is a graph of Raman scattering intensity over a range of Raman shift values for bladder cells collected from urine of three patients afflicted with grade 1 bladder cancer (five lower spectra), and bladder cells collected from urine of four patients afflicted with grade 3 bladder cancer (four upper spectra). The baselines of the spectra are offset to facilitate comparison.
Figure 7:
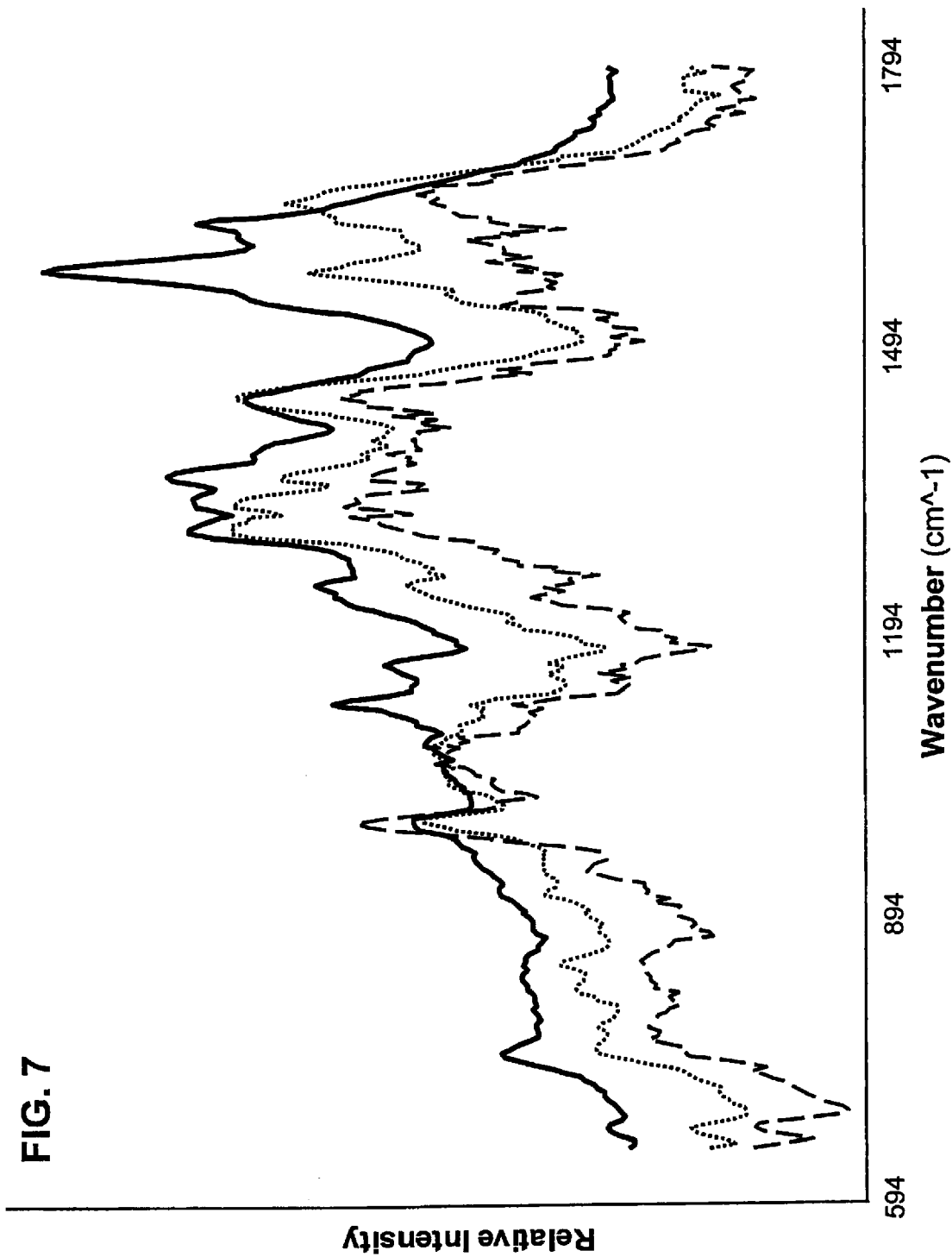
FIG. 7 is a trio of averaged Raman spectra obtained from bladder cells collected from urine of normal patients (dashed line), patients afflicted with grade 1 bladder cancer (dotted line), and patients afflicted with grade 3 bladder cancer (solid line). The baselines of the spectra are offset to facilitate comparison.
Figure 8:
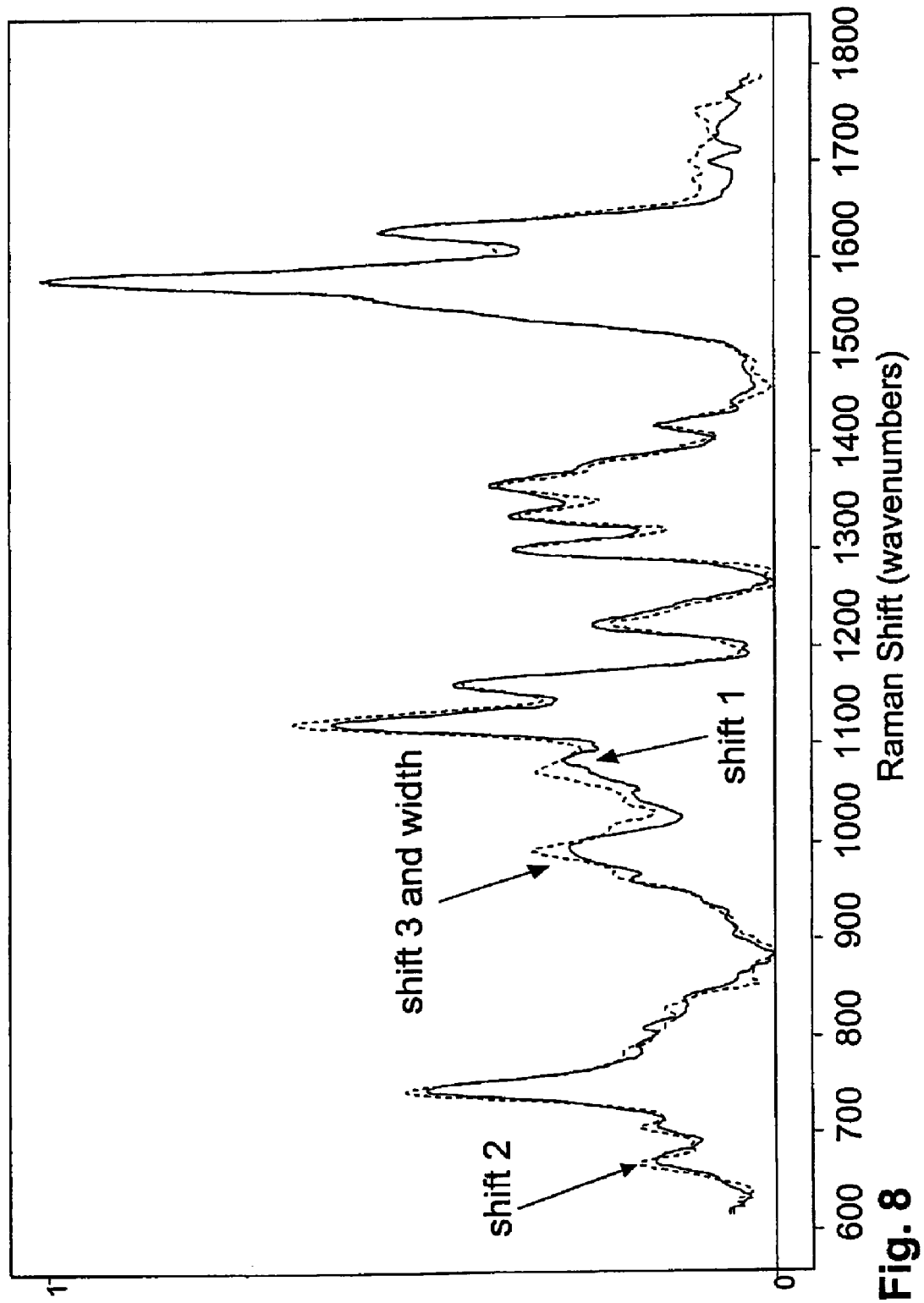
FIG. 8 is a graph of averaged Raman scattering intensity over a range of Raman shift values for normal red blood cells (RBCs; solid line) and for RBCs (including at least one sickled RBC) obtained from a patient with sickle cell disease (dashed line). The Raman spectra for these cells were obtained within 100 milliseconds of the onset of illumination of the cells. Spectra obtained from 16 fields of view, each including 3-5 RBCs, were averaged to produce these data.

It was demonstrated that Raman spectrum of normal bladder cells obtained from urine is significantly different from the Raman spectra of low and high grade malignant bladder cells obtained from urine. These results are shown in FIG. 4. FIGS. 4B, 4C, and 4D are brightfield micrographs of normal, low grade tumor, and high grade tumor bladder cells, respectively. FIG. 4A shows the Raman spectra of these cells. Significant Raman scattering intensity differences (between normal and tumor cells) are observed at approximate Raman shift values of 2900, 1584, 1370, and 1250 $cm^{-1}$. The high and low grade cells have similar spectra, but they exhibit small differences in some spectral regions. As shown in FIG. 5, these differences appear to be significant at Raman shift values of about 2900, 1584, 1370, 1250, and 1100 $cm^{-1}$.

The results described above include Raman spectra which extend over both the so called "fingerprint region" (roughly 28-1800 $cm^{-1}$) and the "CH" region (roughly between 2750 and 3200 $cm^{-1}$). The CH region is often neglected in Raman spectroscopy of biological samples because of the purported lack of specificity and biological relevance of Raman spectral information obtained for this region. The data presented in these figures demonstrate that the proportion of signal in the CH band relative to the fingerprint region varies between cancer and normal samples. Cancer samples tend to have proportionally more scatter in the fingerprint region. By normalizing the spectra such that the area under each curve is the same, this is evident by comparing the heights of the peaks in the fingerprint region to the peak in the CH region, as shown in FIGS. 2 and 3. The value of including the CH region in Raman analysis extends to the imaging paradigm where Raman images of a sample taken in the CH region can be used to ratiometrically standardize fingerprint region information to allow comparison of samples and distinction of signals which represent cancer.

The results shown in FIGS. 4, 5, 6, and 7 demonstrate that Raman scattering data generated as described herein can be used to differentiate bladder cancer cells of different grades. The methods described herein can therefore be used to assess cancer grade in patients and to inform treatment decisions. Combined with superficial and/or microscopic visual analysis, the tumor can be more accurately and thoroughly characterized than was previously possible. The grade determination can also be made more quickly than was previously possible.

Example 2

Raman Scattering Analysis of Red Blood Cells.

Raman molecular imaging (RMI) was used to distinguish normal and sickled human red blood cells (RBCs).

Individual RBCs were obtained from two patients, one of whom was known to be afflicted with sickle cell disease (i.e., homozygous for the sickle cell trait gene) and the other of whom was known not to harbor an allele of the gene for the sickle cell trait. Prior to analysis, RBCs were treated by smearing onto an aluminum-coated glass slide and air dried.

For each RBC, a visual microscopic determination was made of whether the cell was normal (i.e., normally-shaped) or sickled (i.e., sickle-shaped) using a FALCON (TM) Raman imaging microscope obtained from ChemImage Corp. (Pittsburgh, Pa.). A single Raman spectrum was obtained from a field of view that included 3-5 RBCs using the Raman scattering channel of the FALCON instrument. For samples of sickled RBCs, each field included at least one RBC that exhibited the crescent shape characteristic of sickle cell disease. The substantially monochromatic illumination wavelength was 532.1 nanometers, and Raman-shifted scattered light was assessed for RS values in the range from about 600-1800 cm$^{-1}$. Raman spectral data obtained from the RBCs was base-line corrected and smoothed using an a Savitsky-Golay (5-2) algorithm. Baseline correction was performed by fitting a low order polynomial to the spectrum and iteratively adjusting the coefficients of the polynomial to optimize the Raman spectrum.

A succession of Raman spectra were obtained over time for individual RBCs. The first Raman spectrum was obtained within a period of time not exceeding 100 milliseconds after the cell was illuminated. Dynamic changes were observed in the Raman spectra until the cell had been illuminated for at least about 2-5 seconds. A commercial software package (CHEMIMAGE XPERT (TM) from ChemImage Corp., Pittsburgh, Pa.) was used to display, analyze, and compare the Raman spectra.

The data obtained from these experiments are shown in FIGS. 8-11.

Example 3

Raman Scattering Analysis of Cardiac Tissue.

Raman molecular imaging (RMI) was used to assess cardiac muscle tissue and connective tissue in cardiac tissue samples obtained from patients afflicted with either idiopathic heart failure or ischemic heart failure.

Human cardiac tissue samples were obtained from five patients afflicted with ischemic heart failure and from five other patients afflicted with idiopathic heart failure. The tissue samples were obtained in the form of small tissue fragments fractured from explanted hearts which were frozen immediately after removal. Approximately 5 millimeter square tissue fragments were embedded in OCT and sliced into 5-10 micron sections. Tissue slices were placed on an aluminum coated slide. Excess OCT was removed with distilled water. Samples were air-dried and evaluated using a FALCON (TM, ChemImage Inc., Pittsburg, Pa.) Raman microscope.

Each tissue sample was sighted by visible light microscopy a Raman spectrum was obtained from an approximately 25 micron by 25 micron area of the sample. The area from which Raman scattered light was collected included sections of approximately 2-5 cardiac muscle cells (when areas of cardiac muscle were analyzed) or about 625 square microns of intermuscular fibrous material when connective tissue was analyzed. Scarred portions of cardiac tissues obtained from ischemic heart failure patients were excluded from analysis. The visual sightings and Raman scattering determinations were made using a FALCON (TM) Raman imaging microscope obtained from ChemImage Corp. (Pittsburgh, Pa.). The substantially monochromatic illumination wavelength used for Raman analysis was 532.1 nanometers, and Raman-shifted scattered light was assessed for RS values in the range from about 600-1800 cm$^{-1}$. Observations were made on at least three non-contiguous areas representing muscle and intermuscular fiber for each sample. Raman scattered light was collected with a 100× objective.

Raman-shifted scattered light was collected from portions of cardiac tissue which were determined by visible light microscopy to contain substantially only cardiac muscle fibers or substantially only connective tissue. Spectra were obtained from each of these two sub-portions of cardiac tissue samples from the two disease groups.

The data obtained from these experiments are shown in FIGS. 12-15.

Example 4

Raman Scattering Analysis of Kidney Tissue.

Raman molecular imaging (RMI) was used to assess kidney tissue samples of known types using substantially the methods described herein. The data obtained from these experiments are shown in FIG. 17.

Example 5

Raman Scattering Analysis of Prostate Tissue.

Raman molecular imaging (RMI) was used to differentiate cancerous and benign samples of human prostate tissue.

Human prostate tissue samples were obtained from 64 patients afflicted with prostate cancer and from 32 patients not afflicted with prostate cancer. The tissue samples were obtained in the form of frozen surgically excised samples. Pieces of tissue approximately one centimeter square and several millimeters thick were embedded in OCT and sectioned using a cryomicrotome, generating slices which were from 5-10 microns thick. Slices were placed on an aluminum coated slide, and excess OCT was removed with distilled water.

Each tissue sample was sighted by visible light microscopy a Raman spectrum was obtained from an approximately 625 square micron area of the sample. The area from which Raman scattered light was collected included parts from approximately 2-10 prostate cells. The visual sightings and Raman scattering determinations were made using a FALCON (TM) Raman imaging microscope obtained from ChemImage Corp. (Pittsburgh, Pa.). The substantially monochromatic illumination wavelength used for Raman analysis was 532.1 nanometers, and Raman-shifted scattered light was assessed for RS values in the range from about 600-1800 cm$^{-1}$.

The data obtained from these experiments are shown in FIG. 16.

The disclosure of every patent, patent application, and publication cited herein is hereby incorporated herein by reference in its entirety.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A method of assessing the disease state of a mammalian cell, the method comprising:
    irradiating the cell using wide-field illumination with substantially monochromatic light having a wavelength not greater than 695 nanometers;
    assessing a visible light microscopic image of said cell to determine a morphology and a cell type of said cell;
    assessing Raman scattered light produced by said cell at a Raman shift (RS) value characteristic of said cell type, wherein said RS value is selected from the group consisting of RS values in the range from 280 to 1800 cm$^{-1}$ and RS values in the range from 2750 to 3200 cm$^{-1}$, wherein said Raman scattered light is collected using the same objective used to illuminate the cell; and
    comparing the intensity of the Raman scattered light produced by the cell with a reference value corresponding to the intensity of Raman scattered light produced by a reference cell of the same type, whereby the morphology of said cell in combination with a difference between the intensity of the Raman scattered light produced by the cell and the reference value are indicative of the disease state of the cell.

2. The method of claim 1, wherein the cell comprises a prostate cell.

3. The method of claim 1, wherein the cell is not a breast cancer cell.

4. The method of claim 1, wherein the disease state of the reference cell is known.

5. The method of claim 1, further comprising assessing Raman scattered light produced by the cell at a plurality of the RS values.

6. The method of claim 5, further comprising assessing Raman scattered light produced by the cell over a spectrum of the RS values.

7. The method of claim 6, wherein the spectrum includes 650-1800 cm$^{-1}$.

8. The method of claim 6, wherein the spectrum includes 750-1800 cm$^{-1}$.

9. The method of claim 1, wherein the wavelength of the substantially monochromatic light is about 532 nanometers.

10. The method of claim 1, wherein the substantially monochromatic light is generated by a laser.

11. The method of claim 1, wherein the cell is not a red blood cell and is substantially separated from red blood cells prior to assessing Raman scattered light produced by the cell.

12. The method of claim 1, wherein the cell is substantially separated from debris prior to assessing Raman scattered light produced by the cell.

13. The method of claim 1, wherein the cell is a human cell.

14. The method of claim 13, wherein the cell is obtained from a tissue biopsy.

15. The method of claim 14, wherein the tissue is selected from the group consisting of lung, prostate, kidney, colon, bone marrow, brain, blood, and heart.

16. The method of claim 14, wherein the tissue is a lymph node.

17. The method of claim 13, wherein the cell is obtained from a body fluid.

18. The method of claim 17, wherein the body fluid comprises urine.

19. The method of claim 13, wherein the cell is obtained from a fluid that has been contacted with a tissue of the human.

20. The method of claim 19, wherein the fluid comprises peritoneal wash fluid.

21. The method of claim 1, wherein the cell is irradiated in situ in the mammal.

22. The method of claim 1, wherein the cell is irradiated using a laser illumination source for illuminating an area of a sample that includes the cell.

23. The method of claim 22, wherein Raman scattered light produced by the cell is assessed by:
    collecting a Raman spectrum of scattered light from the illuminated area of the sample using an objective and producing a collimated beam therefrom;
    filtering the collimated beam using a liquid crystal tunable filter; and
    collecting the filtered, collimated beam using a detector.

24. The method of claim 23, further comprising storing the output from the detector in a computer memory.

25. The method of claim 1, wherein Raman scattered light produced by the cell is assessed at two sampled RS values, and the ratio of intensities of the Raman scattered light produced by the cell at the sampled RS values is compared with a reference ratio value corresponding to the ratio of intensities of Raman scattered light produced by a reference cell of the same type at the sampled RS values.

26. The method of claim 1, wherein Raman scattered light produced by each of a plurality of cells in a sample is separately assessed.

27. The method of claim 1, wherein assessing said visible light microscopic data includes:
    collecting said visible light microscopic data from an area of a sample that includes said cell along with at least one other cell of a different cell type; and
    distinguishing the cell type of said cell from said different cell type using said visible light microscopic data.

28. The method of claim 1, further comprising:
    correlating said microscopic image from a portion of said cell with the intensity of the Raman scattered light produced by said portion of said cell.

29. A method of assessing the cardiac disease status of a mammalian cardiac cell, the method comprising:
    irradiating the cell using wide-field illumination with substantially monochromatic light having a wavelength not greater than 695 nanometers;
    assessing visible light microscopic data of said cell to determine a location of a cardiac muscle cell;
    assessing Raman scattered light produced by the cell in the location of the cardiac muscle cell at a Raman shift (RS) value selected from the group consisting of RS values in the range from 280 to 1800 cm$^{-1}$ and RS values in the range from 2750 to 3200 cm$^{-1}$;
    wherein said Raman scattered light is collected using the same objective used to illuminate the cell: and
    comparing the intensity of the Raman scattered light produced by the cell with a reference value corresponding to the intensity of Raman scattered light produced by a reference cell of the same type,
whereby a difference between the intensity of the Raman scattered light produced by the cell and the reference value is indicative of the cardiac disease status of the cell.

* * * * *